US006765127B1

(12) United States Patent
Granados et al.

(10) Patent No.: US 6,765,127 B1
(45) Date of Patent: *Jul. 20, 2004

(54) INVERTEBRATE INTESTINAL MUCIN CDNA AND RELATED PRODUCTS AND METHODS

(75) Inventors: Robert R. Granados, Ithaca, NY (US); Ping Wang, Ithaca, NY (US)

(73) Assignee: Boyce Thompson Institute for Plant Research, Inc., Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/294,663

(22) Filed: Apr. 19, 1999

Related U.S. Application Data

(63) Continuation-in-part of application No. 09/103,429, filed on Jun. 24, 1998, now Pat. No. 6,187,558.

(51) Int. Cl.$^7$ .................. C12N 15/09; C12N 15/31; C12N 15/82; A01H 5/00

(52) U.S. Cl. .................. 800/278; 800/288; 800/298; 435/320.1; 435/69.1; 435/419; 435/468; 536/23.7

(58) Field of Search .................. 800/278, 288, 800/298, 205; 536/23.7, 23.5; 435/69.1, 419, 468, 320.1

(56) References Cited

U.S. PATENT DOCUMENTS 5,866,788 A * 2/1999 Kramer et al. .............. 800/205

FOREIGN PATENT DOCUMENTS

| EP | 0 293 249 | 11/1988 | ........... C12N/15/00 |
| WO | WO 96/00783 | 1/1996 | ........... C12N/15/13 |

OTHER PUBLICATIONS

Wang et la. Molecular Cloning and Sequencing of a Novel Invertebrate Intestinal Mucin cDNA. The Journal of Biological Chemistry vol. 272:26 pp. 16663–16669, 1997.*
Linthorst et al. The Plant Cell, vol. 1, pp. 285–291, Mar. 1989.*
Dandekar et al. Plant Science, vol. 96, pp. 151–162, 1994.*
Adang, M. J. and Spence, K. D. (1983) Permeability of the peritrophic membrane of the Douglas fir tussock moth (Oroyia pseudotsugatq). Comparative Biochemical Physiology 75, 233–238.
Barbehenn, R. V. and Martin, N. M. (1995) Peritrophic envelope permeability in herbivorous insects. Journal of Insect Physiology 41, 303–311.
Begon, M.; Daud, K.B.H.; Young, P. and Howells, R.E. (1993) The invasion and replication of a granulosis virus in the indian meal moth Plodia interpunctella: an electron microscope study. Journal of Invertebrate Pathology 61(3), 281–295.

Brandt, C. R., Adang, M. J. and Spence, K. D. (1978) The peritrophic membrane: ultrastrucutural analysis and function as a mechanical barrier to microbial infection in Orgyia pseudotsugata. Journal of Invertebrate Pathology 32, 12–24.
Corsaro, B. G., Gijzen, M., Wang, P. and Granados, R.R. (1993) Baculovirus enhancing proteins as determinants of viral pathogenesis. In "Parasites and Pathogens of Insects vol. 2–Pathogens", pp. 127–145. Academic Press, Inc., New York.
Derksen, A.C.G. and Granados, R. R. (1988) Alteration of a lepidopteran peritrophic membrane by baculoviruses and enhancement of viral infectivity. Virology 167, 242–250.
Faulkner, P.; Kuzio, J.; Williams, G.V. and Wilson, J.A. (1997) Analysis of p74, a PDV envelope protein of Autographa californica nucleoplyhedrosisvirus required for occlusion body infectivity. Journal of General Virology 78, 3091–3100.
Gallo, L. G., Corsaro, B. G., Hughes, P. R. and Granados, R. R. (1991) In vivo enhancement of baculovirus infection by the viral enhancing factor of the granulosis virus of the cabbage looper, Trichoplusia ni (Lepidoptera: Noctuidae) journal o–f Invertebrate Pathology 58, 203–210.
Gijzen, M.; Roelvink, P. and Granados, R. (1995) Characterization of viral enhancing activity from Trichoplusia nj granulosis virus. Journal of Invertebrate Pathology 65(3), 289–294.
Hawtin, R.E.; Zarkowska, T.; Arnold, K.; Thomas, C.j.; Gooday, G.W.; King, L.A.; Kuzio, J.A. and Possee, R.D. (1997) Liquefaction of Autographa californica nucleopolybedrovirus–infected insects is dependent on the integrity of virus–encoded chitinase and cathepsin genes Virology 238(2), 243–253.
Hughes, P.R., van Beek, N.A.M. and Wood, H.A. (1986) A modified droplet feeding method for rapid assay of Bacillus thruingiensis and baculoviruses in Noctuid larvae. Journal of Invertebrate Pathology . 48, 187–192.
Lehane, M.J. (1997) Peritrophic matrix structure and function. Annal Review of Entomology 42, 525–550.
Lepore, L. S., Roelvink, P. R. and Granados, R. R. (1996) Enhancin, the granulosis virus protein that facilitates nucleopolyhedrosis virus (NPV) infections, is a metalloprotease. Journal of Invertebrate Pathology 68, 131–140.
Miller, N. and Lehane, M. J. (1990) In vitro perfusion studies on the peritrophic membrane of the tsetse fly Glossina moristans moristans (Diptera, Glossinidae). Journal of Insect Physiology 36, 813–818.

(List continued on next page.)

Primary Examiner—Medina A. Ibrahim
(74) Attorney, Agent, or Firm—Brown & Michaels, PC

(57) ABSTRACT

The invention represents the disclosure of an insect intestinal mucin (IIM) protein. The IIM protein was been identified and cloned using Trichoplusia ni larva. The cDNA and amino acid sequences have been determined and are disclosed. These sequences are useful for the production of transgenic cells, including plant cells, having insecticidal activity.

7 Claims, 4 Drawing Sheets

OTHER PUBLICATIONS

Miller, N. and Lehane, M. J. (1993) Ionic environment and the permeability properties of the peritrophic membrane of *Glossina moristans*, *Journal of Insect Physiology 39*, 139–144.

Peters, W. and Wiese, B. (1986) Permeability of the peritrophic membranes of some Diptera to labeled dextrans. *Journal of Insect Physiology*. 32, 43–50.

Richards, A. G. and Richards, P.A. (1977) The peritrophic membranes of insects. *Annual Review of Entomology* 22, 219–240.

Sakurada, M.; Morgavi, D.P.; Komatani, K.; Tomita, Y. and Onodera, R. (1996) Purification and characteristics of cytosolic chitinase from Piromyces communis *OTSI*. *FEMS Microbiology Letters*. 137(1), 75–78.

Santos, C. D. and Terra, W. R. (1986) Distribution and characterization of oligomeric digestive enzymes from *Erinnyis ello* larvae and inferences concerning secretory mechanisms and the permeability of the peritroophic membrane. *Insect Biochemsitry* 16, 691–700.

Spence, K. D. and Kawata, M. Y. (1993) Permeability characteristics of the peritrophic membranes of *Manduca sexta* larvae *journal ofInsect* Physiology, 39, 785–790.

Tanada, H. (1985) A synopsis of studies on the synergistic property of an insect baculovirus: a tribute to Edward A. Steinhaus. *journal of Invertebrate* Pathology 45,125–138.

Tellem, R. (1996) The peritrophic matrix, *In* "The Insect Midgut", (M. J. Lehane and P. F. Billingsley, Eds.), Chapman and Hall, London.

Wang, P. and Granados, R.R. (1997a) An intestinal mucin is the target substrate for a baculovirus enhancin. Proceedings of the National Academy of Science, USA 94, 6977–6982.

Wang, P. and Granados, R. R. (1997b) Molecular cloning and sequencing of a novel invertebrate intestinal mucin Cdna. Journal of Biological Chemistry 272, 16663–16669.

Wang, P. and Granados, R. R. (1998) Observations on the presence of the peritrophic membrane in larval Trichoplusia ni, and its role in limiting baculovirus infection. Journal of Invertebrate Pathology, 72, pp 57–62.

Wang, P. Hammer, D.A. and Granados, R. R. (1994) Interaction of enhancin, a viral encoded protein, from the granulosis virus of Trichoplusia ni with the midgut epithelium and peritrophic membrane of four lepidopteran insects. Journal of General Virology 75, 1961–1967.

Wolfersberger, M. G., Spaeth, D. D. and Dow, J. A. T. (1986) Permeability of the peritrophic membrane of tobacco hornworm larval midgut. American Zoologist 26, 76A.

Zimmerman, D. and Mahlan, D. (1976). Water transport across peritrophic membranes of Calliphora erythrocephala–VII. Comparative Biochemistry and Physiology 55, 119–126.

Smith, Matthew D., Antibody Production in Plants, 1996, Biotechnology Advances, vol. 14, No. 3, pp. 267–281.

* cited by examiner

FIG.4

```
II   HP---ALHEPHPD C PPA-EQHWLLPHEVD C TKFYY C EYGLKFIAPAD C APGTEFKFSAQT C WHAALAG C T---LPGPPA-E
IVa        ELLPNG C PADFDIHLLIPHDKY C HLFYD C SHGYTF--EQA C PEGLYFHPYVQA C DSPAHVE C DGEISPAPPUTE
IVb  EDIDIG-DLLDNG C PANFEIDWLLPHGHA C DKYVQ C VHGHLV--ERA C GAGTHFSFELQQ C DHIELVG C T-----LPGGES
IVc  PTEPIEWEPLPHG C PADFSIDHLLPHESO C GQYLQ C VHGQTI--AAP C PGHLHFSPATQS C ESPVTAG C Q--------UFE
VI   PHDPI------HP C VEECHV--LPVAHAD C DKYWV C DGHHQVLVV-- C SEGLQFNPTTKT C DFACHVG C V--------ASH
                       *           ▲                                  ▲
```

INVERTEBRATE INTESTINAL MUCIN CDNA AND RELATED PRODUCTS AND METHODS

REFERENCE TO RELATED APPLICATIONS

This is a continuation-in-part application of parent patent application Ser. No. 09/103,429, filed Jun. 24, 1998 now U.S. Pat. No. 6,187,558. The aforementioned application(s) are hereby incorporated herein by reference.

FIELD OF THE INVENTION

The invention pertains to the field of proteins associated with the peritrophic membranes of insects. More particularly, the invention pertains to a novel invertebrate intestinal mucin cDNA and related products and methods.

BACKGROUND OF THE INVENTION

Vertebrate epithelial organs are covered, throughout the body, with a mucus lining, which serves as a selective physical barrier between extracellular contents and the epithelial cell surface. The mucus lining, especially in the gastrointestinal tract, is highly resistant to various digestive enzymes and provides protection and lubrication for the underlying cells. The protective functions of the mucosal layer are largely dependent upon heavily glycosylated proteins known as mucins. Mucins play an active role in preventing bacterial, viral, and other pathogens from interacting with vertebrate intestinal epithelia.

Mucins are highly O-glycosylated proteins. Carbohydrate moieties on mucins commonly account for more than 50% of the protein by weight. The biochemistry and molecular biology of mucins from vertebrates ha been broadly investigated, with human epithelial mucins being the most extensively studied. Several mucins from humans and other vertebrates have been completely or partially sequenced, and this has contributed to a greater understanding of their structure and function. Full cDNA sequences for human mucin MUC1, MUC2, and MUC7, have been obtained. In addition, mucins from other vertebrates, including mouse MUC-1, rat ascites sialo-glycoprotein-1, canine tracheobronchial mucin, bovine submaxillary mucin-like protein, and frog IIM-A.1, have also been fully sequenced by cDNA cloning.

Studies on invertebrate mucins are very limited in comparison with vertebrate mucins. *Drosophila melanogaster* "glue proteins" from salivary glands have structural characteristics of mucin-like proteins. These "glue protein" have been sequenced but their function has not been fully determined. Mucin-like proteins have also been reported in protozoans. A secretory mucin involved in maintaining the cohesiveness of a clutch of a squid egg-mass formation was identified from that animal's nidamental gland. A glycoprotein from *Drosophila melanogaster* cultured cells was reported to be a mucin-like protein. Recently, a membrane-associated mucin from the hemocytes of *Drosophila. melanogaster* was identified, and a cDNA for the mucin was subsequently cloned. However, to date, there have been no reports on mucins identified from invertebrate digestive tracts.

Part of the reason for this may be that insects do not possess a mucus layer lining the digestive tract and/or other epithelial cells, as do vertebrates. The digestive tract in insects is commonly lined with an invertebrate-unique structure, the peritrophic membrane (PM). PMs are non-cellular matrices composed primarily of chitin, protein, and glycoproteins. PMs demonstrate a protective function similar to the mucus layer in vertebrates (e.g. a selective barrier protecting the digestive tract from physical damages and microbial infections).

Although there are few studies on the interaction between microbial pathogens and PMs, these structures are proposed to serve as a physical barrier to invasion or infection by pathogenic microorganisms. The chitin component of PMs is normally present as a network of chitin fibrils in which proteins and glycoproteins are present. The chitin can be a potential target substrate for intestinal pathogens. This was demonstrated through the degradation of chitin in the PM by a pathogen-encoded chitinase allowing an avian malaria parasite to overcome its mosquito vector intestinal PM barrier and infect the vector itself.

Proteins are the major PM component; however, their functions in the PM are unknown. Studies on the PM proteins are limited to analyses of the amino acid composition of total PM proteins and PM protein profiles as determined by electrophoresis. The only PM protein characterized to date, peritrophin-44, was isolated from *Lucille cuprina* larvae, but its biological function is not fully understood. To date, studies on the interaction of PM proteins with microbial pathogens are limited to the effect of a baculovirus enhancin on lepidopteran PM proteins.

Previous studies have demonstrated that a *Trichoplusia ni* granulosis virus (TnGV) encodes an enhancin protein, a viral enhancing protein, that was identified as a metalloprotease. Enhancin degrades high molecular weight PM proteins in vivo and in vitro. In addition, the protein degradation initiated by these enhancins is correlated with the disruption of the structural integrity of the PM thereby "enhancing" viral infection. It was recently demonstrated that enhancin could degrade high molecular weight PM proteins from several lepidopterous species; however, the chemical nature and function of these proteins in baculovirus pathogenesis were previously unknown.

With a more complete knowledge of the proteinaceous components of the PM, and particularly the mucin-like proteins it will be possible to use that information to enhance the effectiveness of bio-engineered pesticides, recombinant viral vectors, enhance the defenses of transgenic plants, or protect insect vectors susceptible to attack by organisms utilizing enhancin or enhancin-like enzymes.

SUMMARY OF THE INVENTION

Briefly stated the current invention represents the disclosure of a novel intestinal insect mucin comprising two nearly identical isoforms, IIM14 and IIM22 respectively. The proteins are identical except for slightly different peptide length in some repetitive regions, which is common in mucin proteins. This IIM protein has been identified and cloned from *T. ni* larva. Its cDNA and amino acid sequences have been determined and are disclosed. The IIM protein has an approximate molecular mass of 400 kDa. These sequences are useful for the production of transgenic or recombinant vectors including viral, microorganism, cell, plant, or animals, wherein the virus, microorganism, cell, plant, or animal is the product of an insertion of a gene expression vector including a DNA that encodes an IIM protein sequence. Thereafter the engineered host of the IIM DNA sequence is capable of expressing said IIM protein in a functional form. One easily used host is the bacteria is *Escherichia coli*.

Also useful is a purified and isolated recombinant DNA sequence comprising a DNA sequence that codes for an IIM protein. The recombinant DNA sequence used can be a cDNA sequence for either IIM14 or IIM22, SEQ. ID.'s No. 1; and 2 respectively. The current invention also provides for the use of the purified or recombinant proteins, IIM14 or IIM22, SEQ. ID.'s 3 or 4 respectively.

With the cloned IIM sequence it is possible to prepare an IIM protein or peptide by transforming a host cell with an expresssion vector comprising a promoter operatively linked to a nucleotide sequence which codes for a fusion protein wherein said fusion protein comprises a first protein or peptide fused directly or indirectly with a transfer molecule (glutathione-S-transferase), wherein said first protein or peptide is a predetermined protein or peptide of a T. ni IIM protein. Then culturing the host cell under conditions such that the fusion protein is expressed in recoverable quantity. When harvesting the protein or peptide the cells must be collected, isolated, lysed, and the fusion protein purified from the cytosol.

A gene expression vector containing a recombinant DNA sequence encoding a T. ni IIM protein sequence can also be constructed with this technology. This is accomplished through the use of a recombinant plasmid adapted for insertion into and transformation of bacteria or transgenic plants such that these hosts can express either the IIM protein or antibodies to disrupt pertrophic membrane function and formation in larval pests. The antibodies expressed by the plant could bind to the mucin or its ligand or portions the IIM protein could be expressed by the plant to result in competitive binding with the larvae's expressed mucin. As opposed to transformation with the entire IIM sequence, important peptide fragments or functional domains of the IIM protein can individually be transfected into expression vectors.

BRIEF DESCRIPTION OF THE DRAWING

FIG. 4 shows the chitin binding regions of the IIM protein shown in SEQ. ID. NO. 3 and SEQ. ID. NO. 4.

DESCRIPTION OF THE PREFERRED EMBODIMENT

Figure 1:
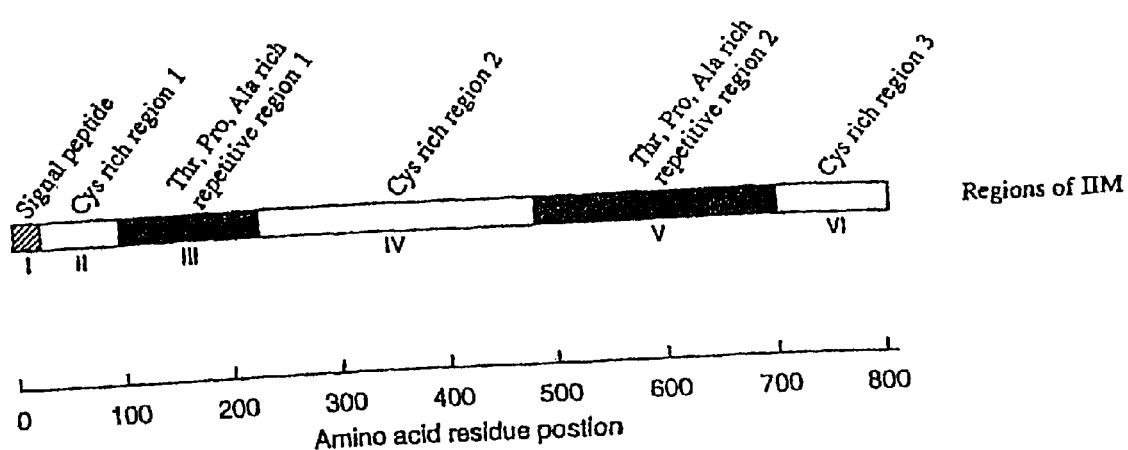
FIG. 1 shows a schematic structure of the IIM protein.

The following detailed description describes the methods used to discover and sequence a novel invertebrate intestinal mucin (IIM), isolate cDNAs encoding this novel mucin, and determine the role of this mucin in the function of the peritrophic membrane during infection by a pathogenic viral organism.

Isolation and Analysis of a Novel Invertebrate Intestinal Mucin

PMs have long been proposed as selective physical barriers in invertebrate intestines. The primary components of PMs include chitin protein and glycoprotein but only one PM protein has been isolated and characterized thus far. PMs in invertebrates is analogous to vertebrate intestinal mucosal components that are secreted by epithelial cells. These vertebrate mucus secretions are composed primarily of one major constituent, intestinal mucin. Intestinal mucins from humans have been broadly studied, and the major human intestinal mucin (MUC2) was fully sequenced. Prior to the present invention, no intestinal mucin had been identified from invertebrates.

The present invention shows a novel invertebrate intestinal mucin (IIM). The novel mucin was first isolated from an insect larvae, T. ni larvae from a laboratory colony reared on a high wheat-germ diet. Midgut PM was dissected from mid-fifth instar T. ni larvae, thoroughly rinsed with de-ionized water, and stored at $-70°$ C. PM proteins were solubilized by boiling PMs in SDS/PAGE sample buffer, and then separated by SDS/PAGE electrophoresis. The IIM protein disclosed herein is a new type of mucin that represents the first intestinal mucin identified from an invertebrate.

To prepare IIM for antiserum production, protein bands can be first visualized by staining the gel with 0.05% Coomassie blue R-250 in 40% methanol followed by de-staining with de-ionized water; this procedure can be followed by excision of the IIM band from the eletrophoresis gel. After equilibration in a SDS/PAGE running buffer, the IIM in the gel slice is electroeluted, and the preparation is purified and concentrated and re-suspended in PBS by ultrafiltration using a centriprep-30 concentrator (Amicon).

For general biochemical analyses, PM protein bands on the SDS/PAGE gel can be initially visualized by copper staining, which facilitates the excision of the IIM band. IIM from this gel slice is also electroeluted after copper ions are removed by washing the gel slice several times in 0.2 M EDTA. Subsequently, the eluted protein preparation is desalted by ultrafiltration.

To isolate and purify the IIM protein for amino acid composition analysis, the sodium phosphate-buffered SDS/PAGE system is used. The gel is stained with copper chloride after equilibration of the gel in 0.375 M Tris-HCl (pH 8.8) with 0.1% SDS. The IIM band is excised and the IIM is recovered by electroelution as described above the preparation is further desalted by extensive dialysis against de-ionized water and then lyophilized.

IIM from T. ni PMs is a 400-kDa protein on 3.5% SDS/PAGE gels. The association of the IIM with PMs is stable over a wide range of pH, in the presence of non-ionic and ionic detergents, and in the presence of protein denaturing reagents. Therefore, very little, or no IIM was present in the supernatants from these treatments. IIM, the predominant PM protein, could be released from the PM by a combination of 2% SDS plus 5 mM DTT, confirming that it was strongly associated with the chitin-containing PM matrix. The IIM was not extracted from the PM by boiling in 2% SDS for 10 min unless a reducing agent was included, demonstrating the presence of intermolecular disulfide bonding in native IIM.

Amino acid composition analysis of IIM, indicated that IIM was rich in threonine (18.7%) proline (16.9%), and alanine (15.9%). These three amino acids accounted for 51.5% of the total amino acid residues in the protein, while aromatic amino acids accounted for less than 5% of the amino acid residues in the protein, and may account for the ability of IIM to by strongly associated to the invertebrate PM chitin fibrils. The IIM amino acid composition profile resembles that of a typical vertebrate mucin that is commonly rich in threonine, serine, proline, alanine, and glycine, and rare in aromatic amino acids.

Quantification of the protein and carbohydrate content of IIM indicated that it was highly glycosylated. Carbohydrate content on IIM accounted for 56% of the total IIM mass, with protein accounting for 44%. Terminal mannose residues and galactose $\beta(1-3)$ N-acetylgalactosamine were detected on IIM by the specific binding of peanut agglutinin and *Galanthus nivalis* agglutinin (GNA). The lectin binding assays using IIM samples pretreated with either O-glycosidase or N-glycosidase showed no binding or significantly reduced binding of the lectins, confirming the positive recognition of G. nivalis agglutinin and peanut agglutinin to IIM. These results demonstrated that IIM has both N-glycosylation and O-glycosylation, since terminal mannose is present in N-linked carbohydrate moieties and galactose βB(1-3) N-acetylgalactosamine is one type of O-linked carbohydrate moiety found in glycoproteins. In addition, removal of the disaccharide, galactose β(1-3) N-acetylgalactosamine by O-glycosidase treatment, resulted in significant reduction (approx. 100 kDa) in the molecular weight of the IIM, further confirming the heavy O-glycosylation on IIM.

The experiments conducted demonstrated the highly protease-resistant nature of the isolated IIM. The stability of the IIM when exposed to degestive enzymes for long periods is aided by the O-linked carbohydrate moieties found in associated glycoproteins. The IIM was highly resistant to endogenous digestive even after a sixteen hour incubation, no degradation of IIM in PMs was observed. However, in the presence of O-glycosidase, IIM was quickly degraded. Control treatments using PMS with inactivated or inhibited endogenous midgut proteases, confirmed that the degradation of IIM in the presence of O-glycosidase was a result of hydrolysis by endogenous digestive proteases, following removal of the protective carbohydrate moiety, galactose β(1-3) N-acetylgalactosamine.

The isolated and sequenced IIM from T. ni PM resembles mammalian secretory mucins in several characteristics, including high O-glycosylation, possible intermolecular cross-linking disulfide bonds, high concentrations of threonine alanine and proline, and resistance to proteases. Selective removal of galactose β(1-3) N-acetylgalactosamine resulted in greatly increased susceptibility to proteolysis indicating that this O-Linked disaccharide plays an important role in protecting the IIM protein from digestive degradation. Unlike vertebrate mucins, insect PM proteins are embedded in a chitin fibril network. The inability to extract the IIM from PMs with various detergents and extreme conditions in the absence of a reducing agent demonstrate that IIM is tightly associated with the chitin-rich PM matrix and that disulfide bonding is seemingly important for this association.

Isolation and Sequencing of a Novel Invertebrate Intestinal Mucin cDNA

The present invention teaches cloned and sequenced full-length cDNAs for IIM from T. ni. IIM has a similar structural organization to human intestinal mucin, MUC2, and is expressed in midgut tissue. Sequence analysis indicates potential chitin binding domains that may interact with the chitin present within the PM.

A cDNA expression library was constructed from T. ni midgut mRNA. Midgut epithelial tissues were dissected from early to mid-fifth instar T. ni larvae in cold Rinaldini's solution. PMs with food contents and other attached tissues (i.e. fat bodies, trachea, and malphighian tubules) were quickly removed from the midgut epithelium. Isolated midgut epithelia were rinsed with cold Rinaldini's solution, quickly frozen in liquid nitrogen, and stored at −70° C. prior to use. Midgut mRNA was isolated using the RNeasy total RNA isolation kit and the Oligotex mRNA isolation kit (Qiagen Inc., Chatsworth, Calif.), according to the manufacturer's specifications. The quality of mRNA was confirmed by Northern blot analysis, which showed no detectable degradation of mRNA after probing with β-tubulin DNA. The cDNA library was constructed from T. ni midgut mRNA using the ZAP-cDNA Gigapack Cloning Kit (Stratagene, La Jolla, Calif.), following the manufacturer's instructions. cDNA was unidirectionally ligated into the Uni-ZAP XR vector (Stratagene, La Jolla, Calif.) between the EcoRI and XhoI sites and packaged with the Gigapack II Gold package extract. The resultant cDNA library was amplified once at 50,000 plaques/15-cm plate in XL1-Blue MRF E. coli host cells.

The library has a complexity of $2.35 \times 10^6$ plaques, of which over 99.5% were recombinants. Screening of the cDNA expression library for IIM cDNA clones was conducted using an IIM-specific polyclonal antiserum in conjunction with the pico Blue Immunoscreening Kit (Stratagene, La Jolla, Calif.), according to the manufacturer's specifications. The first round of screening was performed at a high density (i.e. 50,000 plaques/15-cm plate). Positive plaques were selected and further purified by screening at a low plating density (i.e. 20–50 plaques/10-cm plate). From purified positive phages the pBluescript SK (−) phagemid (Stratagene, La Jolla, Calif.) was excised in vivo following the ZAP-cDNA Gigapack cloning kit protocol.

Screening of the library with the antiserum specific to IIM indicated that the mRNA for the IIM was abundant; 50 positive plaques were obtained from 50,000 plaques. Since only one in three plaques will be in the correct reading frame for protein expression, the frequency of IIM cDNA clones could be 1 in 333. From these 50 plaques, 20 positive plaques were further purified. From these 20 plaques, the pBluescript SK(−) phagemids were rescued by in vivo excision. Following restriction enzyme analysis to map the selected clones, two different full-length clones, pIIM14 and pIIM22, were chosen for sequencing.

Nested deletions from both orientations of the cDNA inserts were constructed using the Erase-a-Base System (Promega Corp., Madison, Wis.). Both strands of the cDNA were sequenced by automated cycle sequencing using T3 and T7 primers, complementary to the pBluescript SK(31) sequences flanking the cDNA inserts. DNA sequence analysis and a data base search were conducted using the DNASTAR software package (DNASTAR Inc., Madison, WD and BLAST data base search programs. Protein O-glycosylation sites were predicted following an O-GLYCBASE search.

The cDNAs from both pIIM14 and pIIM22 were full-length clones, encoding a protein of 788 and 807 amino acid residues, respectively. The nucleotide sequence of each is shown in SEQ. ID. NO. 1 & 2, respectively. The open reading frame in the cDNA from IIM14, was 57 base pairs shorter than in IIM22; otherwise, the open reading frames in these two clones were identical. IIM22 contains a putative polyadenylation signal consensus, AATAAA, located 331 base pairs downstream of the translation stop codon, TAA and 17 base pairs upstream of the poly(A). IIM14 contains a putative polyadenylation signal, AATTAA, located 15 base pairs upstream of the poly(A).

The deduced protein sequences from IIM14 and IIM22 showed a hydrophilicity profile characteristic of a signal sequence at the N terminus of protein sequences. The N-terminal amino acid sequence determined from purified IIM indicated that the cDNA clones encode a protein containing a signal peptide 25 amino acids long and confirmed that the cDNA clones code for the IIM. The amino acid composition of the deduced proteins from IIM14 and IIM22 were very similar to the composition of IIM isolated from T. ni further confirming that the cDNA clones code for the IIM. Protein sequence data reveal that there are four potential N-glycosylation sites. This is in agreement with the biochemical analysis results which demonstrated that IIM has N-linked glycosylation. The amino acid sequence of IIM14 and IIM22 is shown in SEQ. ID. NO. 3 & 4 respectively.

Referring to FIG. 1, the overall IIM sequences can be divided into six distinct regions based upon their sequence features. FIG. 1 shows a schematic structure of the IIM protein. The amino acid composition of each region shows characteristics of a secreted epithelial mucin. Both the N-terminal and C-terminal domains, are rich in cysteine, which accounts for 8.2 and 7.8% of the total amino acid residues, respectively. Region III is rich in threonine, proline, and alanine (49.2, 16.2, and 21.5%, respectively) and contains two types of tandem repeats, TTTQAPT and AATTP, which are typical features for a mucin (6, 32). Region IV is similar to regions II and VI and contains 9.0% cysteine residues. Region V is another threonine, Proline, and alanine-rich section, containing a repetitive sequence, TAAP. This region differed between IIM14 and IIM22 in sequence length, but the sequence features of the IIM protein isomers, and their respective cDNA clones were similar. This region (V), contains 25 TAAP repeats in IIM22.

Northern blot analysis of T. ni midgut RNA with a probe made from IIM22 showed a single band with a molecular size of 3.1 kilobase pairs, indicating that there was no similar polydispersity in IIM transcription, as is found in mammalian mucin transcripts.

Biochemical analysis has shown that IIM from T. ni midgut peritrophic membranes is a novel invertebrate intestinal mucin. The cDNA sequence presented here confirms the identity of this secreted invertebrate intestinal mucin. The overall structural organization of IIM is similar to human intestinal mucin, MUC2, which can be described as follows: (a) as a secreted mucin, the IIM contains a 25-amino acid signal peptide at the N terminus (region I); (b) relative to MUC2, which has two different tandem repeat domains interspersed by a cysteine-rich region that distinguishes MUC2 from other mucins, IIM also contains two threonine-rich tandem repeat regions (regions III and V) where potential O-glycosylation sites are located; and (c) the two tandem repeat regions are flanked by cysteine-rich regions (regions II, IV, and VI) (FIG. 1).

In comparison with MUC2, which contains more than 5100 amino acid residues, the apoprotein in IIM is relatively small. The mature IIM contains either 763 or 782 amino acid residues. Prediction of O-glycosylation using the O-GLYCBASE search program indicated that 127 of the 147 threonine residues and 5 of the 23 serine residues in IIM22 (excluding the signal peptide) were potential O-glycosylation sites. In regions III and V, all threonine residues, except the two at the boundaries of region III (at position 99) and region V (at position 486), were potential O-glycosylation sites. There is only one threonine in the non-tandem repeat domains (at position 314) marginally predicted as a potential O-glycosylation site. A PROSITE data base search using DNASTAR demonstrated four tentative N-glycosylation sites. All four sites were located within region V.

Regions III and V contain high levels of threonine, alanine, and proline, and do not contain any aromatic or sulfur-containing amino acids, which is similar to the corresponding domains in MUC2. IIM contains multiple repeating units. These repeating units are short compared with those found in mammalian mucins. Region III contains two tandem repeating sequences, TTTQAPT and AATTP, throughout the whole region. Region V contains an even shorter repeating unit, TAAP. The repeating units in this region are dispersed at four potential N-glycosylation sites and several other locations. Sequences TTVT(V/S)PP and TTAVPEI occur frequently in the disrupted locations in region V. The repeating sequences in IIM did not exhibit similarity to any known repeating sequences from other mucins.

The difference between cDNAs IIM14 and IIM22 is in region V. In this region, IIM14 contains 19 fewer amino acids than IIM22, which could be due to genetic polymorphism, as reported for human and other vertebrate mucin genes. Both IIM cDNAs contain G+C-rich repeated sequence units in region III and V. These G+C-rich rich repeated sequences (with χ-like sequence features), could be responsible for the evolution of genetic polymorphisms. This difference between IIM14 and IIM22 could also be the result of alternative splicing during RNA processing. Such a phenomenon has been observed in mucin gene expression. The AG at position 2005 and 2006 in IIM22 could potentially serve as a 3'-splicing site, which would lead to a mRNA corresponding to IIM14.

The protein sequence features of the IIM are in agreement with the data from the biochemical analysis of IIM. The presence of N-glycosylation motifs and mucin-characteristic threonine-rich tandem repeats in the IIM sequence confirmed the presence of N-glycosylation and extensive O-glycosylation of IIM, previously analyzed by carbohydrate-specific lectin binding and specific glycosidase analyses.

Cysteine-rich domains are common in mucins and have been demonstrated to cause oligomerization of mucins by disulfide bonding. These cysteine-rich regions might also contain globular structures with intramolecular disulfide bonds. These protein regions could become exposed once the disulfide bonds are reduced. Disulfide bonds in the non-heavily O-glycosylated regions of IIM are involved in maintaining a digestive protease-resistant structure. However, protein sequence analysis did not show significant sequence similarity between the cysteine-rich regions in IIM and the cysteine-rich regions from MUC2, or other mammalian mucins. This is not surprising, since insects are phylogenetically very distant from mammals and since IIM is a constituent of a unique invertebrate chitin-containing structure.

IIM is tightly associated with the PM, and is a major structural constituent of the PM. These results indicate that IIM may have a high affinity to the chitinous fibril network of PMs. By computer-assisted sequence analysis, a protein fragment in region IV was aligned to two chitin binding domains in chitinases from a yeast, *Saccharomyces cerevisiae*, and a fungus, *Rhizopus oligosporus*. In addition to region IV, sequences in regions H and VI also show a certain degree of similarity to the chitin binding domains described above; however, the levels of similarity were lower than that found in region IV. In a recent report, a non-mucin insect PM protein from *Lucilia cuprina*, peritrophin-44, showed binding capability to chitin, but it did not show significant sequence similarity to known chitin binding sequences. However, the cysteine-rich domains with peritrophin-44 shared the same structural feature, a six-cysteine-containing sequence present in cysteine-rich domains in chitinases.

Surprisingly, the sequence features of IIM in the cysteine-rich regions are similar to what Elvin et al. proposed for peritrophin-44. Almost all sequences in regions II, IV, and VI are composed of such a six-cysteine consensus. This result supports the conclusion that IIM may tightly bind to the chitin network of PM in the non-glycosylated cysteine-rich regions. The strong binding of IIM to chitin could be a very important factor for the formation of PMs in invertebrates and aid in the stability of the chitin network. Based on the structural characteristics of IIM and the strong binding associated with uM and chitin, it is likely that the chitin fibrils in PMs are protected from enzymatic degradation by IIM. Considering the biochemical properties of IIM and the putative chitin binding sequences in non-glycosylated regions in IIM, the IIM protein backbone is protected from degradation in the hydrolytic enzyme-rich midgut environment by two different mechanisms: (a) the densely O-glycosylated regions (regions III and V) are protected by oligosaccharide moieties; and (b) the cysteine-rich non-glycosylated or less glycosylated regions (regions II, IV, and VI) are protected by disulfide covalent bonding forming a "buried" structure or by the protein binding to chitin in the PM. The mucin nature and chitin binding capability of IIM can explain the high resistance of IIM to midgut digestive enzymes and the protective functions of PMs in invertebrates, especially in insects, Any reagents with the potential effect of damaging IIM, such as baculovirus enhancins or reducing agents, will result in the destruction or attenuation of the protective role of the PM against parasites and other microorganisms.

Localization of Expression of the Mucin in the Peritrophic Membrane

By immunolocalization in tissue sections, it was determined that IIM is expressed in midgut tissues.

The IIM from *T. ni* larvae was localized by immunocytochemistry with the antiserum to IIM. An antiserum to IIM was generated by immunizing a Flemish Giant/Chinchilla Cross rabbit with purified IIM from *T. ni* PMs. Preimmune serum from the rabbit was collected and used as a control for immuno-detection of IIM. Fourth instar *T. ni* larvae were fixed in 4% paraformaldehyde overnight at 4° C. and embedded in paraffin. After tissue sectioning and de-waxing immunostaining was performed as follows: sections on glass slides were blocked for nonspecific staining with 3% bovine serum albumin in phosphate-buffered saline, followed by incubation with antiserum against IIM in phosphate-buffered saline containing 3% bovine serum albumin. After incubation with the first antiserum, the sections were washed with phosphate-buffered saline and incubated with a secondary antibody against rabbit IgG conjugated with colloidal gold (Sigma). Following secondary antibody incubation and subsequent washing, the sections were fixed with 2.5% glutaraldehyde. Immunogold staining was intensified by silver enhancement using the Silver Enhancer kit (Sigma). The immunostained sections were counterstained with hematozylin and eosin and examined by microscopy.

Microscopic observations showed that IIM was localized in the peritrophic membrane and in the area surrounding the midgut epithelial brush border. Observation at a high magnification demonstrated that IIM could be secreted from goblet cells of the midgut epithelium. Immunostaining with preimmune serum from the same rabbit used to generate the anti-IIM antiserum did not show any positive reaction. In addition to the midgut, positive staining was occasionally observed in malpighian tubules on the lumen side. To verify whether this occasional positive staining in malpighian tubules was specific to IIM and to test whether IIM was present in other tissues, a Western blot analysis of extracts from various tissues of *T. ni* larvae using anti-IIM antiserum was conducted.

Tissues were isolated from fifth instar *T. ni* larvae and rinsed with phosphate-buffered saline. The tissues were then homogenized and boiled in 0.0625 M Tris-HCl (pH 6.8) containing 2% SDS, 5% Beta-mercaptoethanol, and 10% glycerol. Undissolved materials were removed by centrifugation. Protein concentrations in the supernatants were estimated using the Bradford protein assay. One microgram of protein from each tissue extract, except for the PM extract, for which 0.04 $\mu$g of protein was used, was loaded onto the gel. Proteins were separated by SDS-PAGE, followed by blotting onto Immobilon membrane (Millipore Corp., Bedford, Mass.), and probed with anti-IIM antiserum.

The Western blot analysis showed that IIM was primarily present in the non-cellular PM. A broad band at 200 kDa could also be detected in the PM extract when this sample was overloaded. This band is considered a degradation product of IIM by active midgut digestive enzymes, since the PM moved through the digestive tract. The midgut was the only tissue in which a significant amount of IIM was detected. Besides the IIM band, some lower molecular weight bands were also present in the midgut extract. These bands possibly were the IIM protein in the process of glycosylation but not yet fully glycosylated. The extract from malpighian tubules did not show any positive staining at the gel position for IIM. Some weak positive staining was detected in the extract from hemolymph with a major broad band between 66 and 97 kDa. Salivary gland, fat body, and epidermis extracts did not show any positive reaction to the anti-IIM antiserum. The bands detected in the malpighian tubules and hemolymph did not show the correct molecular weight corresponding to IIM, and the reactivity to the anti-IIM serum was very low. Therefore, the proteins represented by these bands do not indicate the presence of IIM in tissues other than the PM.

Localization of IIM by immuno cytochemistry indicates that IIM is primarily expressed in the midgut tissue and is likely to be secreted by goblet cells. Interestingly, this is similar to the secretion of mucins by goblet cells in vertebrate intestinal epithelium.

Peritrophic Membrane Secretion Patterns of Invertebrate Intestinal Mucin

*T. ni* PM first appears in larvae before feeding starts and is present along the entire length of the mesenteron. IIM plays a significant role in the formation and function of the peritrophic membrane. To ascertain the secretion patterns of IIM, PM structure and secretion patterns were examined in the anterior, middle and posterior regions of the mesenteron.

Third instar larvae were allowed to fed on diet up to 24 hours. Prior to dissection, larvae were placed in wax filled Petri dishes, stretched and pinned through the head capsule and telson, using pins held with forceps. The larvae were then flooded with cold fixative (3.2% formaldehyde, 5% glutaraldehyde in 0.1 M Sorensen's phosphate buffer, pH 7.2 containing 3% sucrose) and dissected to remove the cuticle. The exposed alimentary canal was fixed for 2 hours at 4° C., washed in 0.1 M Sorensen's phosphate buffer containing 3% sucrose for 2 hours, post-fixed in 1% osmium tetroxide in 0.1 M sodium cacodylate buffer, washed in double distilled water (ddw), stained en bloc for 4 hours with 2% aqueous uranyl acetate (on ice), washed in cold ddw for 0.5 hour, and then dehydrated in an ascending ethanol series from 50 to 100%. The specimens then were infiltrated with a 1:2 mixture of ethanol: Spurr's resin for 1 hour, followed by a 1:1 mixture for 2 hours, and lastly placed in 100% Spurr's resin overnight. The specimens in resin were embedded in molds and cured for 60° C. for 24 hours.

Other specimens also were embedded in LR White resin for immunocytochemical procedures. Dissections were performed as above except the fixative contained 4% paraformaldyde and 0.5% glutaraldehyde in 0.1 M phosphate buffer saline (PBS), pH 7.2. Freshly dissected alimentary canals were fixed in this solution overnight, incubated in 0.1 M ammonium chloride in PBS for 1 hour, washed in PBS for 2 hours, and dehydrated in ascending ethanol series from 50 to 100%. The specimens were resin infiltrated with a 1:1 LR White: ethanol mixture for 2 hours, transferred to 100% resin with one change, and kept overnight to allow complete resin infiltration. The specimens in resin were loaded into gelatin capsules and allowed to polymerize at 50° C. overnight Thick sections (0.5 $\mu$m) were cut using glass knives on Reichert Ultramicrotome. For transmission electron microscopy (TEM), thin sections were cut using a diamond knife and mounted on naked or formvar-coated nickel grids and observed on a Phillips EM 201 transmission electron microscope.

For wheat germ agglutinin (WGA) staining, thin sections were incubated for 1 hours at room temperature in blocking buffer [0.01 M PBS (pH 7.2) containing 1% cold water fish gelatin, 0.075% Tween 20, and 0.075% Triton X-100] and subsequently incubated in a 1:100 dilution of 20 nm gold-labeled WGA (20 $\mu$/ml) (E-Y Laboratories, San Mateo, Calif.) in blocking buffer for 1 hour. After incubation, grids were washed with PBS, ddw and stained with uranyl acetate (UA) and lead citrate (PbC). Cytochemical controls consisted of addition of 1 part 10 MM chitotriose with 1 part WGA solution at twice the above concentration.

Invertebrate intestinal mucin (IIM) was localized in thin sections which were first blocked in blocking buffer then incubated in a 1:300 dilution of anti-IIM preparation for 1 hour. Sections were then washed in multiple changes of blocking buffer for 1 hour then incubated in 1:100 dilution of 20 nm gold conjugated goat anti-rabbit IgG (E-Y Laboratories, San Mateo, Calif.) for 1 hour. Sections were then washed with blocking buffer, PBS, ddw and stained with UA and PbC. Cytochemical controls were first incubated in a 1:300 dilution of rabbit preimmune serum for 1 h, washed in PBS for 1 hours and incubated in secondary antibody as described above. Scanning electron microscopy (SEM) was performed on T. ni larvae. The midgut and PM were dissected and placed in Karnovsky's fixative for 2 hours. The specimens were then dehydrated in an ascending ethanol series from 70 to 100%, critical point dried, fixed to aluminum stubs with silver paste, sputter coated with gold-palladium, and viewed in an AMR-100A scanning electron microscope.

PM was present along the entire length of the mesenteron. In the most anterior midgut region examined, PM appeared as a single thin structure located between the stomodeal valves and midgut epithelium. Slightly posterior to this region (about 2 mm) PM appeared slightly thicker. This slight increase in thickness may be the result of the association of fine thread-like material to the delaminated PM. In the middle region of the mesenteron, the morphology of the PM changed to a more robust structure composed of compact layers. Similar in appearance to PMs located in the middle portion of the mesenteron, PM in the posterior mesenteron (just adjacent to the proctadeaum) can be seen at lower magnifications partitioning dietary plant cell walls and microbes from the underlying midgut epithelium.

Observations taken from electron micrographs shows PM formation begins with the appearance of fine fibrous-like material within the brush border of the anterior mesenteron. These nascent PMs first appear in the upper third of the microvillar brush border as diffuse structures. Probing these regions with anti-IIM and WGA-gold, produce discrete lines of labeling confined to these fibrous-like structures. These staining patterns indicate IIM and chitin (or N-acetyl-D-glucosamine containing structures) to be present in the nascent PM. This same binding pattern can be seen at the tips of the microvillar brush border demonstrating that nascent PM moves apically for delamination into midgut lumen. These delaminated PMs have a fibrous appearance and bind both WGA-gold and anti-IIM. Scanning electron microscopy (SEM) of the anterior midgut region revealed a microvillar brush border inundated with various amounts of material. Interestingly, SEM apparently captured individual secretion events where PM was resting above cells. At higher magnifications, these newly delaminated PMs possessed fibrous-like material, which is mostly obscured by smooth matrix material. Finally, these individual secretion events coalesce form a large smooth and continuos PM which now conceals the underlying midgut epithelium.

To determine when PM first appears within the midgut lumen, third instar and newly molted third instar larvae were examined for the presence of PM. Although PM was not found in the pharate stage, there was localization of anti-IIM within the brush border (data not shown). Examination of newly ecdysed larvae (which have just passed their exuviae across the telson) showed a well-developed PM within the middle part of the midgut. In these larvae, the anterior midgut showed the presence of diffuse material packed between the interstices of microvilli. This material labeled extensively with anti-IIM and was present in the gut lumen above newly secreted PM. Interestingly, there was an association of this diffuse material to delaminated PMs. Finally, the staining patterns of IIM were investigated through out the length of the mesenteron. Cells located in the anterior midgut possessed vesicles, which were extensively labeled with anti-IIM. In the posterior regions, anti-IIM localized to microvillar brush border to columnar epithelial cells adjacent to goblet cells. This same phenomenon was observed in the brush border of cells from the middle portion of the mesenteron.

At the entrance of the mesentron, the PM was observed as a thin structure sandwiched between the tips of the microvillar brush border and intima of the stomodeal valves. This delicate-looking membrane increased in thickness as is it moved in a posterior direction toward the proctodaeum. The delamination of PM from the microvillar brush border was only observed in the anterior mesenteron. No PM delamination events were seen in the middle or posterior mesenteron. Furthermore, sections representing the mid- and posterior mesenteron showed no discrete lines of labeling within the brush border when probed with anti-IIM or WGA-gold. This observation demonstrates that chitin and IIM do not aggregate to form nascent PM in regions past the anterior mesenteron. Within the anterior mesenteron, PM formation begins with the secretion of chitin and matrix material (IIM). These PM components appear to first aggregate within the upper part of the brush border to from a nascent PM. This is followed by delamination of PM into the midgut lumen. Even though PM delamination events appears to be restricted to the anterior mesenteron, there is secretion of IIM from cells located in the middle and posterior midgut. In the middle and posterior mesenteron, the majority of anti-IIM localized to the brush border. Secretion of IIM through out the entire length of the mesenteron may account for the observed increase in PM thickness. Interestingly, IIM secretion was often localized to columnar epithelial cells directly adjacent to goblet cells.

Our observations that PM formation is restricted to the anterior part of the midgut is consistent with previous studies. In one study, the European corn borer (ECB, Ostrinia nubilalis) larval PM formation was found to be limited to the anterior mesenteron. In this region, ECB nascent PM was embedded within the brush border and stained with WGA-gold (indicating the presence of chitin containing structures). Even though the authors were able to determine an anterior site of chitin substructure assembly and delamination, they were unable to directly determine where protein matrix was synthesized and secreted. The current disclosure demonstrates that the midgut region is responsible for the secretion of protein matrix in *T. ni* larvae. By probing the midgut for the major protein moiety IIM, it was determined that the chitin substructure and protein matrix (IIM) apparently are secreted together from cells located within the anterior part of the mesenteron. These results are consistent with the SEM observations which show fibrous linear structures (assumed to be chitin microfibrils) embedded in a proteinaceous matrix. Finally, another very interesting observation is the secretion of IIM through out the mesenteron. This whole midgut secretion phenomenon may provide additional amounts of matrix material to damaged PMs. This may in turn preclude microbes and rough dietary components access to the midgut epithelium.

The Role of the Mucin in the Function of the Peritrophic Membrane and Baculovirus Infection A baculovirus enhancin, which is encoded and carried by specific baculoviruses, has mucin-degrading activity both in vitro and in vivo. The in vivo degradation of IIM by enhancin was correlated with the enhancement of baculovirus infections in insects. These findings show that viruses have evolved a novel strategy to overcome intestinal mucinous barriers against microorganisms by utilizing a mucin-degrading enzyme.

Incubation of IIM with TnGV enhancin showed that the enhancin had activity against IIM. To demonstrate proteolytic activity by TnGV enhancin against IIM, purified IIM was incubated with 1.25 μg/ml TnGV enhancin in 0.05 M Tris-HCl buffer (pH 7.5) containing a cocktail of protease inhibitors minus the metalloprotease inhibitor, EDTA at 37° C. for 3 hours or overnight. The degradation of IIM was examined by SDS/PAGE analysis. A parallel treatment of IIM without enhancin was included as a control. The degradation products of IIM displayed a banding pattern similar to that observed during incubation of intact PMs with enhancin. To confirm the metalloprotease nature of enhancin, IIM was incubated with TnGV enhancin in the presence of 10 mM EDTA. The addition of 10 mM EDTA to the incubation buffer blocked the digestion of the IIM and confirmed the metalloprotease nature of enhancin.

In vivo IIM degradation assays with *T. ni* neonate larvae demonstrated that enhancin degraded IIM in the midgut of living insects and that the degree of degradation appeared to be dose-dependent. Two in vivo assays were developed to include neonate and fifth instar *T. ni* larvae, based on the methods employed to determine the efficacy of an enhancin on virus infections. The in vivo neonate IIM assay and a concomitant virus bioassay were conducted by feeding *T. ni* neonate larvae with inoculum droplets containing $10^5$ occlusion bodies/ml of AcMNPV and varying doses of TnGV enhancin, as described by Wang et al. Following ingestion of the inoculum, 25 larvae from each treatment were transferred onto artificial diet, incubated at 28° C. for 90 minutes, and collected for Western blot analysis using an antiserum specific to IIM. For Western blot analysis, the larvae were homogenized in 100 ul of SDS/PAGE sample buffer. Subsequently, 4 μl of each sample was electrophoresed through a 7.5% SDS/PAGE gel, blotted, and then probed with anti-IIM antiserum.

To assess the correlation between the extent of IIM degradation in living insects and the degree of enhanced AcPV infection by TnGV enhancin, 60 neonate larvae from each feeding group were also collected and individually reared on artificial diet. Viral infections were monitored and examined throughout the whole insect larval developmental stages, as described by Wang et al. The extent of degradation of IIM was correlated with increased AcMNPV infection in larvae. This enhanced mortality was statistically significant and can be presented by the regression analysis: Probit mortality=4.72+0.256× enhancin dose (ng/larva) ($R2=99.2$; $P=0.004$).

The in vivo IIM degradation assay was also conducted by feeding fifth instar *T. ni* larvae with TnGV enhancin and analyzing the residual IIM in the fecal pellets. Early fifth instar *T. ni* larvae were fed 10 ul of inoculum containing 5% sucrose, 10 μg/ml blue food coloring, and 5 μg TnGV enhancin in 25 mM sodium carbonate buffer (pH 10.5). Afterward, the larvae were transferred to individual rearing cups containing artificial diet and incubated at 28° C. During the incubation period, enhancin will digest the IIM present in the PM. PMs are secreted within the intestine and later excreted with fecal pellets, which are normally ensheathed within the remnants of a PM. The first three fecal pellets marked with blue food coloring therefore were collected and subjected to Western blot analysis using the IIM-specific antiserum. The in vivo IIM-degradation assay using fifth instar larvae showed that IIM was present in the control fecal pellets and exhibited some minor degradation. However, no IIM was detected in the fecal pellets collected from the TnGV enhancin-fed larvae, confirming that enhancin completely degraded IIM in the digestive tract of living insects.

The presence of an IIM protein and its degradation by enhancin is not restricted to the species, *T. ni*. Another mucin, similar to the IIM from *T. ni* PMs, was also isolated from *Pseudaletia unipuncta* PMs and biochemically characterized. This mucin is also degraded by the TnGV enhancin and degradation was correlated with enhanced baculovirus infections in *P. unipuncta* larvae.

The PDV that crossed enhancin treated *T. ni* PMs was infectious, as was demonstrated by increased mortality rates compared to control treatments (Table 1). The effect of enhancin on PM permeability to infectious viruses was confirmed using a second insect species, *P. unipuncta*. Enhancin had a significant effect on PM permeability, although the *P. unipuncta* PMs appeared to be more permeable to the virus (Table 1).

In lepidopterous larvae, the PM is a structure containing pores which may vary in size among different insect species. Low level permeability of untreated *T. ni* PMs to blue dextran 2000 appears to confirm the presence of naturally occurring pores within the PM matrix. Although the purpose of this study was not to determine the approximate pore size of *T. ni* or *P. unipuncta* PMs, these studies did show that control *T. ni* PMs were permeable to blue dextran (diameter: 54 nm) but were almost impermeable to AcMNPV PDV (186 nm diameter×357 nm length) over an 8-hour period. Insect bioassays also suggested that untreated *P. unipuncta* PMs probably had a larger pore size and allowed passage of more PDV particles than PMs from *T. ni* since control mortality values were higher for samples obtained from *P. unipuncta* PM permeability experiments (1% vs. 38%, respectively; Table 1).

TABLE 1

T. ni neonate bioassays showing increased permeability of T. ni and Pseudaletia unipuncta peritrophic membrane to AcMNPV PDV following treatment with enhancin.

| Treatment | T. ni Peritrophic Matrix[a] | | | P. unipuncta Peritrophic Matrix[b] | | |
|---|---|---|---|---|---|---|
| | Total Insects Tested | Avg. % Mortality ± SE | t-Test (p) | Total Insects Tested | Avg. % Mortality ± SE | t-Test (p) |
| PM[c] enhancin treated | 90 | 15.6 ± 2.9 | <0.01 | 150 | 90.7 ± 2.9 | <0.01 |
| PM control | 90 | 1.0 ± 0.3 | | 150 | 38.0 ± 8.2 | |
| AcMNPV PDV control | 90 | 97.8 ± 2.2 | | 150 | 100 ± 0 | |

[a]Summary of 3 independent tests.
[b]Summary of 5 independent tests.
[c]PMs mounted in a dual chamber permeability apparatus were treated with 3 mg/ml enhancin for 1 hour and samples were collected 16 hours post-treatment.

Our work showed that sephacryl-purified enhancin preparations contain traces of contaminating insect proteases. In a subsequent study, Lepore et al. (1996) showed that extensive purification of enhancin by ion exchange chromatography and immobilized α-macroglobulin removed the contaminating proteases without diminishing the in vivo and in vitro activity of enhancin, thus providing evidence that these proteases did not have a role in the enhancement of infections. Furthermore, in that same study, Lepore, et al. (1996) also demonstrated that purified TnGV enhancin, expressed by a recombinant AcMNPV in insect cells, was active on insect PMs.

Addition of protease inhibitors provided evidence that potential contaminating proteases did not have a role in increasing the PM permeability. The metalloprotease inhibitor EDTA was able to inhibit the action of enhancin. Although there is no published evidence that granulosis viruses encode a chitinase, it was recently reported that such a functional gene was present in the nuclear polyhedrosis virus, AcMNPV. To rule out the effect of any possible chitinase contamination in our enhancin preparation a potent chitinase inhibitor was used and no effect on the ability of enhancin to increase PM permeability was found. Chitinase activity was not detected in our preparations using a chitinase activity assay.

Previous studies with enhancin suggested that the PM, though clearly not an impenetrable barrier, does reduce the exposure of susceptible midgut cells to baculoviruses. It appears that some insect viruses may have evolved similar mechanisms to degrade the structural integrity of the PM and facilitate the passage of infectious virus. Derksen and Granados (1988) reported that an unidentified factor in the polyhedrin fraction of AcMNPV was able to affect the protein profile and structure of the PM. This observation was recently confirmed by Faulkner et al. (1997) who found that OBs (Declusion bodies) from both a mutant and wild-type AcMNPV could degrade the PM from T. ni larvae. Furthermore, the presence of an enhancin-type gene was recently reported from Lymantria dispar nuclear polyhedrosis virus suggesting that other similar nuclear polyhedrosis viruses (NPVs) may carry enhancin genes. Begon et al. (1993) reported Plodia interpunctella GV (PiGV) OBs caused dramatic and significant effects of the PM structure from the same species and concluded that the PM provided a barrier to PiGV infection at lower virus doses.

Although there have been many investigations concerning the mode of action of enhancin, prior to the work of inventors consensus has not been reached. It was previously reported that an enhancin from PuGV acted on the plasma membrane of midgut cells and cultured insect cells, facilitating the entry of virus particles into the cells by providing attachment sites or facilitating membrane fusion for the virus particles. Based upon the work described in this patent application, the inventors believe a major role of GV enhancins is to disrupt the structural integrity and increase the permeability of the PM to baculovirus particles. Our previous studies demonstrated that enhancin from TnGV digested a specific major PM protein, insect intestinal mucin. The digestion of this PM mucin and the resulting degradation of the PM structure was correlated with enhanced baculovirus infection of insect larvae. It is reasonable to conclude that the disruption of the PM structure resulted in the increased porosity of the PM, thereby facilitating the infection of the underlying epithelial cells. Thus, these viral-encoded proteins appear to play an important role in baculovirus pathogenesis.

T. ni PMs are present in all larval instars and at all stages between molts. Therefore, IIM may play a protective role throughout the entire larval period. No mucin degrading protease has been previously reported to be associated with a virus to assist the penetration of a pathogen through a mucinous protective barrier; therefore, this study represents a novel concept in animal virus pathogenesis. The present invention enables further studies on the specific recognition sites and cleavage of mucins by baculovirus enhancins, and the biological properties of IIM and enhancing. Furthermore, use of IIM degrading enzymes in recombinant plants or baculoviruses will decrease larval growth and increase the pathogenesis of virus infections.

Having discovered the IIM protein and its function, the inventors were able to develop applications for use of the novel cDNA sequences and the recombinant protein.

Diet Incorporation Experiments Using Anti-IIM Serum

Polyclonal antibodies against an insect peritrophic membrane (PM) protein from the Australian blowfly, Lucilia cuprina inhibited growth and caused mortality of blowfly larvae. It was reported that this biological response was caused by the PM antibody, which blocked nutrient diffusion across the PM. The present invention includes the discovery that a polyclonal antibody against the T. ni PM mucin (IIM) has an adverse effect on T. ni growth and survival.

Mucin was prepared from T. ni fifth instar larval PM by preparative PAGE. The gel was stained by $CuCl_2$ (0.3M) for 5 min and the band containing mucin was isolated and destained in 0.2 M EDTA. Mucin was further eluted from the gel slices by electroelution, and used to immunized rabbit following a standard rabbit immunization protocol. 0.2 mg mucin was used per injection for a total of 3 injections. Serum was collected at 6 weeks after the first injection and IgG was purified from the serum using caprylic acid and ammonium sulfate methods (Harlow, E. & Lane, D. 1988—Antibody, a laboratory manual. Cold Spring Harbor Laboratory). Control rabbit IgG was also purified from normal rabbit serum (Gibco).

A laboratory colony of T. ni reared on high wheat germ diet was used in these experiments. To prepare diet incorporated with IgG, high wheat germ diet was prepared but with less water (10% less than the final diet volume). After mixing all the components, the diet was a allowed to cool gradually to 45° C., and IgG solution was added with vigorous stirring. Heat inactivation experiments showed that the immunoreactivity of the anti-IIM serum was reduced above 60° C. (data not shown). Water was added when necessary to adjust the volume. The diet prepared in this way has exactly the same concentration of each component as normal high wheat germ diet, with the exception of the addition of IgG. The final concentration of IgG in the diet was 20% of the original IgG concentration (V/V) in original anti-IIM serum. The diet was aliquoted (2.5 mls/cup) into 1 oz cups which was sufficient diet to allow the larvae to develop into pupae.

*T. ni* neonates were placed individually into the cups with standard (no IgG) or IgG-incorporated diet. This time point was designated as time zero. The larvae were incubated at 28° C. and the larval growth was recorded every 8 hours. The larval weight was also recorded at the 3rd and 6th day. Pupal weight was measured when all the larvae had pupated. The experiment was conducted twice with 30 insects per treatment.

Incorporation of IgG into the diet had a significant effect on *T. ni* larval development (Table 2). Although control rabbit IgG containing diet had a strong effect on larval growth compared to larvae on standard wheat germ diet, the anti-IIM IgG treatment had an even stronger and statistically significant effect. The duration of growth from neonate to pupa was delayed in anti-IIM IgG fed larvae, and was significantly longer than control IgG containing diet fed larvae. Similarly, the anti-IIM IgG fed larvae had the lowest weight at day 3 and day 6, and their weight was also significantly lower than larvae fed on control IgG diet at day 6 in both experiment and at day 3 for experiment 2. No difference in pupal weight was found between all the treatments in both experiments.

The control rabbit IgG had a significant effect on larval development, compared with larvae growing on standard high wheat germ diet. Several different commercial rabbit sera were compared (two batches from Sigma, and one from Gibco), and they all showed a similar effect on *T. ni* development. The reason for this is not clear. No major cross-reaction of normal rabbit IgG to *T. ni* peritrophic membrane components was detected in western blot experiments. It is possible that IgG somehow interferes with the digestive physiology of the insect, or has some feeding deterrent effect. A 20 similar phenomena was also reported by Casu et al. (1997) where the growth of the blood feeding insect, *Lucilia cuprina* was inhibited in the presence of high concentration of normal control IgG.

The design of the experiments conducted were effected by the relatively low amount of serum that can be obtained from rabbits (i.e.,70 mls/rabbit) for use in experiments. Using a PM permeability chamber it was also demonstrated that anti-IIM serum could block the permeability of the PM to particles smaller than 5 mn. This demonstrates that such a phenomenon, if it occurred in vivo, might have a detrimental effect on the nutritional physiology of the insect. These data demonstrates that the delivery of anti-IIM antibodies through transgenic plants is a novel approach for affecting insect development or mortality.

Altered In Situ Peritrophic Membrane Permeability

The present invention includes the discovery that feeding larvae anti-IIM IgG affects the permeability of the peritrophic membrane.

Fifth instar larvae reared on a high wheat germ diet were starved for 1 hours. Starved larvae were then injected per os

TABLE 2

Comparison of *T. ni* larval and pupal weights and developmental duration from neonate to pupa.

| Treatment | # of insect | Duration from Neonates to Pupae (hr ± SE) | p* | Larval Weight at Day 3 (mg ± SE) | p* | Larval Weight at Day 6 (mg ± SE) | p* | Pupal Weight (mg ± SE) | p* |
|---|---|---|---|---|---|---|---|---|---|
| Exp. 1—Control | 30 | 201.47 ± 1.71 | | 6.45 ± 0.49 | | 142.50 ± 7.35 | | 225.57 ± 3.43 | |
| Exp. 1—Normal IgG | 30 | 212.48 ± 2.78 | 0.05 | 3.91 ± 0.33 | 0.11 | 93.65 ± 6.93 | 0.01 | 221.16 ± 2.94 | 0.62 |
| Exp. 1—Anti-IIM IgG | 30 | 219.07 ± 1.79 | | 3.28 ± 0.19 | | 72.47 ± 4.23 | | 223.28 ± 3.10 | |
| Exp. 2—Control | 30 | 193.6 ± 1.46 | | 5.78 ± 0.30 | | 167.17 ± 6.26 | | 223.83 ± 3.21 | |
| Exp. 2—Normal IgG | 30 | 206.90 ± 2.91 | 0.02 | 3.99 ± 0.24 | 0.02 | 112.93 ± 9.39 | 0.03 | 224.20 ± 3.04 | 0.45 |
| Exp. 2—Anti-IIM IgG | 30 | 216.53 ± 2.82 | | 3.17 ± 0.24 | | 88.94 ± 6.82 | | 227.70 ± 3.29 | |

*From t-test comparing weight or duration between larvae on normal IgG diet and anti-IIM IgG diet.

An effect of anti-IIM IgG on *T. ni* larval development was observed. Compared with larvae fed on control rabbit IgG containing diet, the larvae on anti-IIM IgG containing diet required a longer time to develop from a neonate to pupa, and had a lower larval weight at day 3 and day 6. In most cases, the differences were statistically significant. Since no difference in pupal weight for the various treatments was observed, the differences in larval weight might be caused by a difference in speed of development. It is clear that the presence of anti-IIM IgG in the diet resulted in significantly slower growth of *T. ni* larvae. Anti-IIM IgG binds to the major protein on the insect peritrophic membrane, which could result in the blockage of nutrient flow through the peritrophic membrane.

with 20 μl of anti-IIM IgG (2× concentrated) solution and placed on a high wheat germ diet containing an equivalent of 20% anti-IIM IgG and 4% (dry wt) FITC-Dextran (3.2 nm diam.). Controls larvae were injected per os with either PBS or normal serum IgG and placed on their respective diets. After feeding for 2.5 hours at 28° C., larvae were chilled on ice and dissected under saline buffer to expose the alimentary canal. Once the esophagus and proctodeaum were ligated, a small hole (0.2×2 mm) was made to expose the PM. This hole was made in the middle portion of the midgut just immediately anterior to the anastomosing malpighian tubules. These mesenterons were then severed from the alimentary tract and placed in a small dish which contained 15-ml buffer. To help remove any free FITC-dextran, the ligated midgut was rinsed 3 times with 15-ml aliquots of buffer. When the final rinse solution was removed, the ligated midgut was re-suspended in 4 ml of saline buffer and incubated under gentle mixing. Aliquots of incubating solutions were removed every 0.5 hours and measured for the amount of fluorescence using a fluorescent plate reader set at a 485-nm excitation of 530-nm emission.

Figure 2:
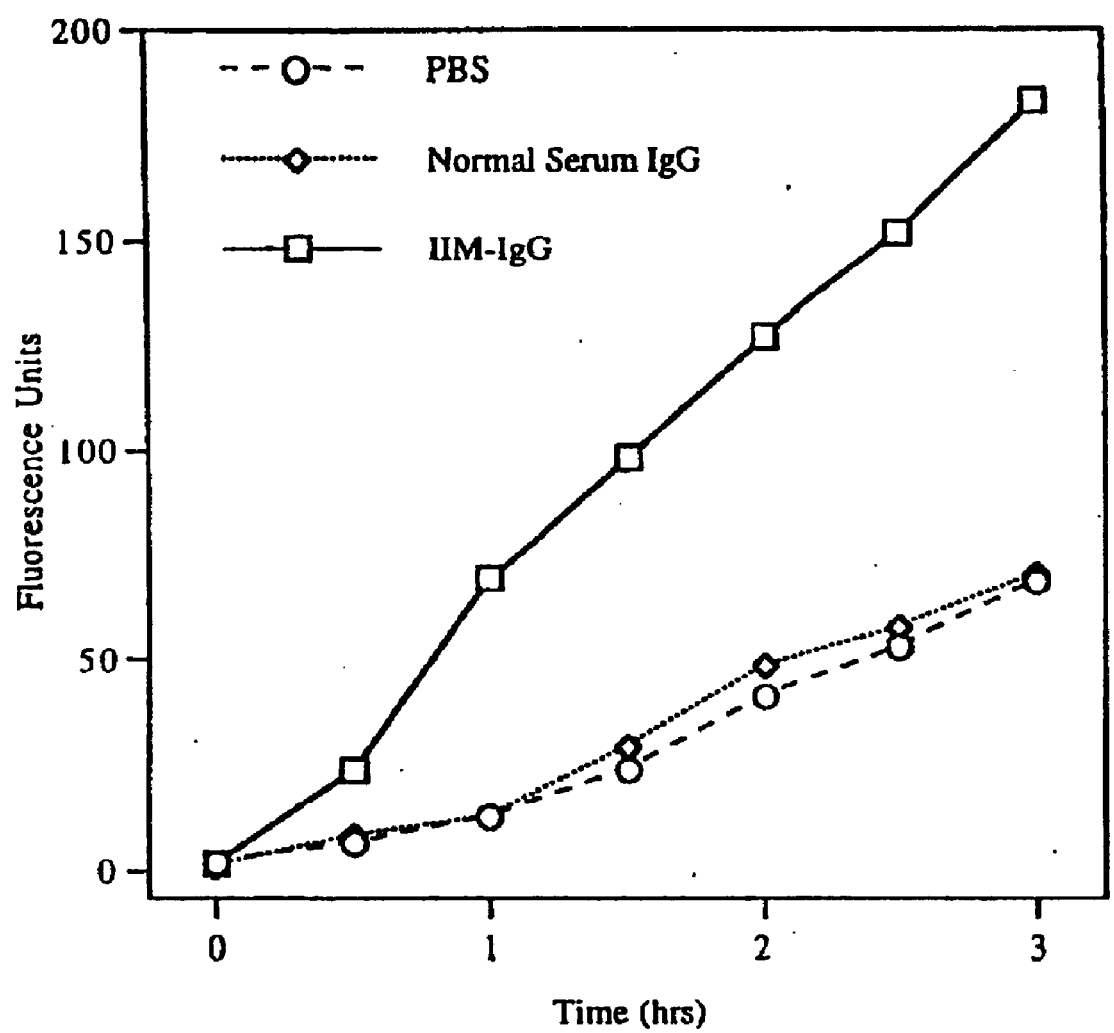
FIG. 2 shows that greater amounts of FITC-dextran (3.2 nm dia) diffused across the peritrophic membrane of ligated T.ni alimentary canals taken from larvae fed on IgG containing diet for 2.5 hours.
Figure 3:
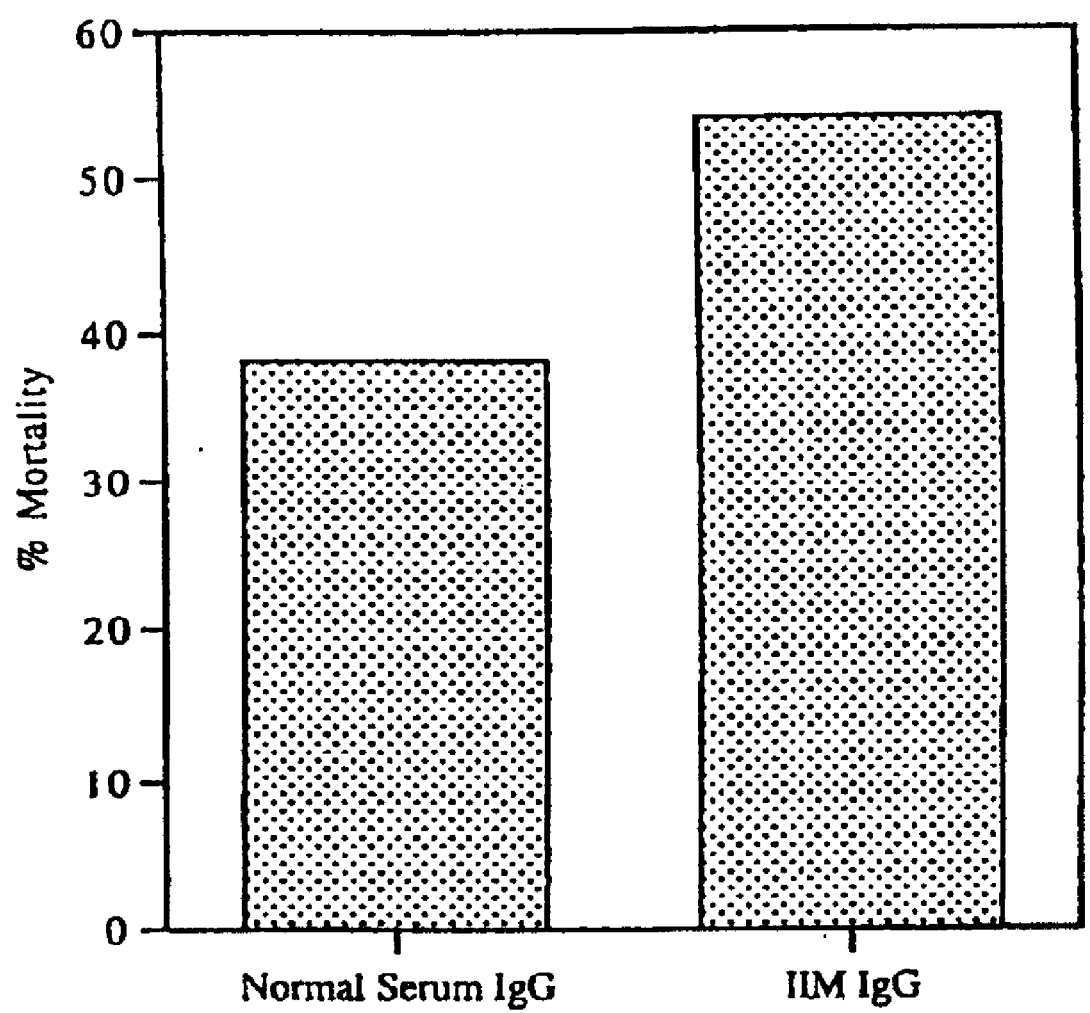
FIG. 3 shows that the presence of IgG increased larval mortality due to AcMNPV infection.

The permeability characteristics of PMs to passage of FITC-dextran is presented below. *T. ni* larvae fed on diets containing IIM-IgG showed greater amounts of FITC-dextran in the incubating buffer as compared to those larvae fed on diets containing normal serum and PBS (FIG. 2). Intact, lighted midgut showed FITC-dextran is confined within the midgut proper and that the midgut wall acts as a barrier to the 3.2 nm FITC-dextran.

FIG. 2 shows permeability characteristics of ligated midgut from larvae fed diet containing either IIM-IgG, normal serum IgG, or PBS. An intact, ligated midgut showed low passage of FITC-dextran across midgut wall. There was more FITC-dextran present in the incubation buffer of IIM-IgG ligated midgut. Each treatment and control are replicated.

In contrast, insect larvae that have fed on diets containing IIM-IgG have a greater PM permeability to FITC-dextran. The final amount of fluorescence in the incubating medium (at 3 hours) was greatest from IIM-IgG fed insects. One possible explanation for this is that ingested IgG may bind to newly secreted IIM thus altering the amounts of protein matrix available for normal PM synthesis. These results are contradictory when compared to the blocking ability of anti-IIM to passage of FITC-destran in the in vitro studies of peritrophic membrane permeability. In those in vitro studies, PMs were dissected and treated with serum. In the in vivo studies, insects are fed IIM-IgG for 2.5 hours. Therefore, IgG may bind to delaminated PM resulting in a "short term blockage" which could be followed by a subsequent "long term structural alteration" of PM. PM alterations could result from antibody competing for IIM (especially during PM formation). These interactions could produce very porous PMs. IIM-IgG induced PM structural abnormalities may be an appropriate explanation for the observed weight changes and increased development time of larvae from the diet incorporation experiments.

Thus, the use of IIM anti-serum against larval pests would first block the insects ability to absorb nutrients and then dramatically increase the infection rate of ingested baculoviruses due to the increased permeability. Furthermore, this disruption effect can be caused by antibodies expressed by a transgenic plant binding to IIM or expression of portions of the IIM by the plant that competively bind to the peritrophic membrane.

Effect of IIM IgG on AcMNPV Infection

Based on the observations that IIM IgG may interfere with PM structure, a virus bioassay was conducted to determine if the ingestion of IIM IgG along with AcMNPV would increase larval mortality due to viral infection. A neonate droplet bioassay was conducted as reported by Lepore et al. (1996) except IgG replaced enhancin. *T. ni* neonates consumed approximately 1 occlusion body and 10 nl of IgG solution profied from normal rabbit serum or anti-IIM serum. After droplet consumption, neonates were placed on high wheat germ diet and monitored for mortality due to AcMNPV infection. In two preliminary experiments there was a trend in increased mortality (but not significant) of those neonates which consumed IIM IgG as compared to those fed normal serum IgG as shown in FIG. 3. This shows that the administration of virus with IIM IgG will increase insect mortality and can be an important strategy in the suppression of insect damage.

Ubiquity of Mucins in Insect Species

*T. ni* mucin or IIM is an integral peritrophic membrane or matrix (PM) protein. IIM with its cysteine rich domains, apparently binds chitin to form a strong semipermeable structure which partitions ingested food and microbes from the midgut epithelium and may aid in digestion. The inventors examined the distribution of mucin (IIM) in different insect species.

TABLE 3

| Common name | Genus species | Family | Cross Reactivity with anti-IIM |
|---|---|---|---|
| Cabbage looper | *T. ni* | Noctuidae | yes |
| Armyworm | *Pseudaletia unipuncta* | Noctuidae | yes |
| Tobacco budworm | *Heliothis virescens* | Noctuidae | yes |
| Black cutworm | *Agrolis ipsilon* | Noctuidae | yes |
| Beet armyworm | *Spodoptera exigua* | Noctuidae | yes |
| Fall webworm | *Hyphantria cunea* | Arctiidae | yes |
| Banded woollybear | *Pyrrharctia isabella* | Arctiidae | yes |
| Imported Cabbageworm | *Pieris rapae* | Pieridae | ? |
| Common white butterfly | *Pieris napi* | Pieridae | no |
| Silkworm | *Bombyx mori* | Bombycidae | yes |
| European corn borer | *Ostrinia nubilalis* | Pyralidae | yes |
| Monarch butterfly | *Danus plexippus* | Danaidae | yes |
| Gypsy moth | *Lymantria dispar* | Lymantriidae | yes |
| Potato tuberworm | *Phthorimaea operculella* | Gelechiidae | yes |
| Diamondback moth | *Plutella xylostella* | Plutellidae | yes |
| House fly | *Musca domestica* | Muscidae | yes |
| Tarnished plant bug | *Lygus lineolaris* | Miridae | yes |
| Sweet potato whitefly | *Bemisia tabaci* | Aleyrodidae | yes |
| English grain aphid | *Sitobion avenae* | Aphididae | yes |
| American cockroach | *Periplaneta americana* | Blattidae | yes |
| German cockroach | *Blattella germanica* | Blattellidae | yes |
| Fruitfly | *Drosophila melanogaster* | Drosophilidae | ? |
| Yellowfever Mosquito | Aedesaeqypti | Culicidae | ? |
| Fungus gnat | Bradysia ssp. | Sciaridae | no |
| Colorado potato beetle | *Leptinotarsa decemlineata* | Chrysomelidae | no |
| Western spotted cucumber beetle | *Diabrotica undecimpunctata* | Chrysomelidae | no |
| Mealybug | *Planococcus citri* | Pseuclo-coccidae | no |

Insect midgut was dissected to remove the PM. PM proteins were solubilized in SDS sample buffer containing mercaptoethanol. Supernatants were subjected to SDS-PAGE, blotted onto nitrocellulose membranes, probed with a polyclonal anti-IIM antibody preparation, washed, and incubated in a secondary antibody labeled with alkaline phosphatase. Bands were visualized by the addition of NBT/BCIP solution to the blots.

Seventy-six percent of the insect species tested (16/21) possess protein or protein moieties which cross reacted with anti-IIM antibody. Table 1 lists the insect species tested for the presence of mucin. PMs were examined in all insects except for mealy bugs and sweet potato whitefly where the whole insect was used. Only midguts of Lygus bugs were extracted and examined for the presence of IIM.

Examination of blots showed the presence of strong to weak signals. Immunoreactive band development was strong in the tobacco budworm, fall armyworm, banded woollybear, armyworm and cabbage looper. The remainder (listed below) gave moderate, weak or no cross reactivity to anti-mucin antibody. Also, some insects had high molecular weight bands similar in size to *T. ni* IIM (denoted by asterix)

| Strong Band Development | Weak Reactivity |
|---|---|
| *Tobacco budworm | *European corn borer |
| *Fall armyworm | *Monarch butterfly |
| *Banded Woollybear | American cockroach |
| *Armyworm | Beet armyworm |
| *Cabbage Looper | No Reactivity |
| Moderate Reactivity | Imported cabbageworm |
| *Black cutworm | Mealybug |
| *Gypsy moth | Fungus gnat |
| House fly | Colorado potato beetle |
| German cockroach | |
| Tarnished plant bug | |
| Diamondback moth | |
| Potato tuberworm | |
| Whitefly | |

*possess bands which are around 400 kD

These studies have demonstrated that mucin (IIM) or mucin-like PM proteins are present in a wide variety of insect species in 5 orders. These insects and possibly many other species may share common mechanisms which involve mucin or mucin like proteins which bind chitin thus permitting the formation of PM. It is interesting to note that a Homopteran and a Hemipteran possess discrete bands which cross-react with anti-IIM antibody. This is interesting observation since these insects may not produce a PM as found in other insects. Some investigators feel these insects may produce extracellular secretions that may be functional analogues to the chitinous PM. Based on our observations, there may exist in Homopterans and Hemipterans a protective barrier present which contains mucin-like proteins.

Two potential relevant applications exist to this work. First, the insects which cross react with anti-IIM may be sensitive to the PM degrading molecule enhancin. Second, these same insect PMs may be susceptible to antibody binding which would reduce nutrient assimilation thus leading to a pre-reproductive growth or death.

Chitin Binding and Its Potential As an Insecticidal Target

Plant lectins, which are carbohydrate binding proteins, have been tested for their insecticidal activity against many insect species and some show promise for use in transgenic plants. The mechanism for this anti-insect activity is not known but is believed to be mediated by lectin binding to chitin in the PM or by interacting with glycoproteins on the midgut epithelial cells. Wheat germ agglutinin (WGA) is a chitin specific lectin and others have shown that in the European corn borer, Ostrinia nubilalis, WGA could bind to the chitin in the midgut and interfered with PM formation. Such interference resulted in an altered and discontinuous PM structure, which allowed the food content to penetrate through the PM protective barrier. Our recent ultrastructural studies on the PM formation in *T. ni* larvae have shown that chitin is always co-localized with IIM in the midgut. These immunocytochemical studies showed that nascent PMs were initially delaminated as chitin containing fibrils from the anterior region of the midgut and subsequently, the major protein (IIM) was added to the PM matrix.

Calcofluor is a fluorescent dye with high chitin binding affinity. It has been utilized in studies on the formation of fungi and algal cell walls which are protective structures containing chitin and proteins. Calcofluor interferes with the cell wall formation by binding to nascent chitin molecules during cell wall formation, thus blocking chitin fibril assembly. Similar investigations on insect midgut chitin fibril formation using the chitin binding agent Calcofluor had not been approached until our recent studies were carried out. Our studies have shown that Calcofluor can be used to extract and solubilize chitin binding proteins from dissected *T. ni* PMs. These isolated proteins have high chitin binding properties and are normally not extractable from fully formed PMs by detergents or extreme pH conditions. Calcofluor fed to *T. ni* larvae completely inhibited and/or disrupted PM formation. We believe that this phenomenon is due to the disruption of chitin fibril formation by the binding of Calcofluor to nascent chitin molecules as observed in other organisms.

This PM disruption/inhibition phenomenon was further verified in *Lymantria dispar, Pseudaletia unipuncta, Helicoverpa zea,* and *Hyphantria cunea*. Elegant studies with plant fungal systems which used dye compounds including Calcofluor showed that chitin biosynthesis and assembly was probably disrupted. We believe that binding of Calcofluor to the PM chitin blocked the interactions among chitin molecules and/or the binding between chitin and newly synthesized PM proteins, and severely interfered with PM formation. Feeding *T. ni* larvae with an artificial diet containing 1% Calcofluor (a concentration used by most investigators) resulted in insect mortality and significantly slowed the growth of the treated larvae. As expected the disruption of PM formation by Calcofluor resulted in significantly increased baculovirus infections in the larvae.

This same phenomenon of increasing virus infection was first observed by others; however, the mechanism of action on the insect PM was not determined until now. Our studies on the effect of Calcofluor on PM formation has uncovered a unique mode of action of this chitin binding agent in the insect midgut. These findings confirm our hypothesis that targeting the chitin in the insect midgut by chitin binding peptides can affect PM formation or its properties, causing significant disruption of midgut physiology and function. If these chitin targeting molecules are shown to have possible insecticidal properties, the genes for chitin binding peptides will serve as new genetic tools for use in recombinant microorganisms and transgenic plants.

Our current studies have demonstrated that PM proteins strongly bind to the chitinous PM matrix and such binding is critical for the PM formation and its function. Sequence analyses of *T ni* IIM and other PM proteins have shown that these midgut proteins contain multiple putative chitin binding domains as follows:

Amino Acid Position (See SEQ. ID. NO. 3 & 4
   IIM region II—amino acid 26 to 98
   IIM region IVa—amino acid 243 to 315
   IIM region IVb—amino acid 320 to 392
   IIM region IVc—amino acid 408 to 478
   IIM region VI
      IIM 14—amino acid 695 to 757
      IIM 22—amino acid 714 to 776
Nucleotide Position(See SEQ. ID. NO. 1 & 2)

IIM region II
  IIM 14—nucleotide 113 to 331
  IIM 22—nucleotide 101 to 319
IIM region IVa
  IIM 14—nucleotide 767 to 982
  IIM 22—nucleotide 755 to 970
IIM region IVb
  IIM 14—nucleotide 995 to 2013
  IIM 22—nucleotide 983 to 2001
IIM region IVc
  IIM 14—nucleotide 1258 to 1471
  IIM 22—nucleotide 1246 to 1459
IIM region VI
  IIM 14—nucleotide 2120 to 2308
  IIM 22—nucleotide 2165 to 2353

To isolate these chitin binding domains, one can express *T. ni* IIM in insect cells using a recombinant baculovirus. Construction of recombinant baculoviruses to express foreign proteins is a routine technique. To construct the recombinant baculovirus, one clones the IIM cDNA into a baculovirus expression transfer vector which utilizes the polyhedrin gene promoter to express the IIM (e.g. pBlueBac4.5 from Invitrogen). Recombinant baculoviruses can be generated by cotransfection of insect cells with the constructed transfer vector and linearized Autographa californica nuclear polyhedrosis virus DNA (e.g. Bac-N-Blue AcN/fNPV DNA from Invitrogen). The IIM can be expressed in the high recombinant protein producing cell line, HighFiveTM (Invitrogen). The suitability of the insect cell expression system for IIM expression can be confirmed by assaying the chitin binding activity of the insect cell-expressed IIM to regenerated chitin. Briefly, insect cells infected with the recombinant AcN/fNPV are lyzed with a non-ionic detergent, such as Triton X-100 and sonication. The cell lysate is clarified by centrifugation and incubated with regenerated chitin to let IIM bind to the chitin. The chitin/protein complexes are thoroughly washed with buffer and isolated by centrifugation. Chitin bound IIM are released with a SDS/B-mecaptoethanol sample buffer and subsequently analyzed by SDS-PAGE and Western blot analysis with an anti-IIM antiserum. A similar approach was used for a mosquito PM protein which was over expressed in insect cells and demonstrated to have chitin binding activity.

The chitin binding regions can be confirmed by a biochemical approach. *T. ni* IIM can be over expressed in insect cells using a baculovirus expression vector and bound to regenerated chitin following the procedures described above. Following the binding reaction, the chitin/IIM complexes are washed with buffer to remove unbound IIM and contaminant proteins. Our current studies on isolated native *T. ni* PM proteins have shown that these proteins have chitin binding activities and the proteins/chitin complexes are strongly bound and resistant to washing with stringent buffers (e.g. 20 mM acetic acid or 1%SDS). Controlled proteolysis with protease K of the chitin bound IIM is performed to selectively degrade non-chitin-binding regions of the IIM. Chitin bound fragments are isolated as protein/chitin complexes by centrifugation and subsequent washing with buffer and then solubilized with a SDS/mecaptoethanol-containing sample buffer. The chitin bound fragments with an expected low molecular weight (chitin binding domains) are analyzed by SDS-PAGE (15% to 20% gels) to separate individual fragments. These fragments are subsequently isolated and subjected to N terminal protein sequencing by microsequence analysis. Based on the amino acid sequences derived from the chitin bound fragments, it is possible to design and synthesize peptides to test their chitin binding activities. Competitive binding assays of IIM to regenerated chitin with synthetic peptides as competitors can be conducted to determine the chitin binding activities of these synthetic peptides.

In order to determine the conserved amino acid residues important for chitin binding, one can design synthetic peptides based on published conserved sequences in addition to the identified chitin binding domains above. Putative chitin binding sequences have been identified by sequence analysis in several PM proteins from different species (Elvin et al., 1996; Wang and Granados, 1997; Schorderet et al. 1998; Shen and Jacobs-Lorena, 1998) and these sequences are similar. Based on these reported sequences one can design synthetic peptides with a mutation to these conserved amino acid residues to identify and establish the conserved amino acid residues responsible for the strong chitin binding activity.

The chitin binding domains in IIM can also be identified by making deletions and mutations of the IIM gene. One can express truncated and mutated IIM proteins in insect cells using a baculovirus expression vector. The truncated IIM cDNA fragments are prepared using polymerase chain reactions (PCR) using oligonucleotide primers flanking the desired cDNA fragments. These primers are designed to contain suitable restriction enzyme digestion sites so that the amplified cDNA fragments can be easily cloned in frame into the expression vector. Truncated proteins are transiently expressed by transfecting insect cells (e.g. High FiveTM cells) with the expression vectors. Chitin binding activities of the expressed proteins will be assayed by their incubation with regenerated chitin followed by analyses of the chitin bound proteins by SDS-PAGE and Western blotting using an anti-IIM antiserum.

IIM fragments can be expressed in insect cells as intracellular proteins and be released from cells by solubilization with a nonionic detergent such as Triton X-100 and by sonication. The chitin binding activities of the expressed peptides are assayed by incubation of the cell lysates with regenerated chitin in an Eppendorf tube followed by washing of the chitin by centrifugation. Subsequently, the chitin bound peptides is analyzed by SDS-PAGE and Western blot analysis with an anti-IIM antiserum. If assays using whole cell lysates results in high cell protein background, one can construct an expression vector containing a secretion signal peptide at the N-termini of the peptides to be expressed. In such a way, one can obtain the expressed peptides from serum free cell culture medium, thereby minimizing contamination with cellular proteins. Alternatively, one can construct a vector containing a polyhistidine tag fused to the cDNA inserts. PolyHistidine fused peptides can be isolated using a metal charged agarose resin (e.g. Probond Metal Binding Resin from Invitrogen) before chitin binding assays are conducted.

One can use the fragments to identify and evaluate amino acid residues necessary for chitin binding activity by substitution of these candidate residues. Amino acid residue substitution is accomplished following site directed mutagenesis of the cloned cDNA fragments for chitin binding domains. Oligonucleotides containing a mutated site are generated and mutant clones are obtained using a site directed mutation kit (e.g. GeneEditor in vitro site-directed mutagenesis system from Promega). Mutated chitin binding domains are expressed in insect cells and their chitin binding activities are assayed. Such assays will identify specific residues necessary for chitin binding.

Identified chitin binding domains can be over-expressed as chitin binding peptides in *E coli* using an *E coli* expression vector, such as PRSET expression vector series (Invitrogen), to determine if *E. coli* expressed peptides have chitin-binding activities. The over expressed peptides carries a fused polyHistidine tag so that these chitin binding peptides can be easily isolated using nickel-charged agarose resin. Tests of chitin binding activities of *E. coli* expressed peptides are performed using the chitin binding assay described above. If the expressed peptides show chitin binding activities, this provide an efficient and economical system for production of these chitin binding peptides for use in biological studies.

Chitin binding peptides can also be over expressed in an eukaryotic system using insect cells and recombinant baculovirus vectors. cDNA fragments coding for chitin binding peptides are cloned into a baculovirus expression transfer vector which utilizes the polyhedrin gene promoter to express polyHistidine fusion proteins (E.g. pBlueBacHis2 series from Invitrogen). Recombinant baculoviruses are generated as described above. Expressed chitin binding peptides are isolated using a nickel-charged agarose resin.

Anti-IIM Antibody and Serum Production

To isolate an Anti-IIM antibody serum, IIM is purified by solubilizing *T.ni* PM in SDS buffer containing mercaptoethanol according to the extraction procedure described in the literature (Wang and Granados, *Proc. Natl. Acad. Sci U.S.A.*, 97, 6977–6982). The solubilized PM proteins are subjected to SDS-PAGE and bands are visualized by copper staining. The band containing IIM is cut from the gels, destained and electro-eluted. To help remove SDS from proteins, elutant will be loaded on a column containing AG-1-X2 resin (Biorad). The elutant is lyophilized leaving the concentrated protein. Generally, 1000 PMs yields 30 µg of purified IIM.

To obtain large amounts of serum goats are used and inoculated with IIM protein antigen. A similar technique has been used by Casu et al. (*Proc. Natl. Acac. Sci. U.S.A.*, 94, 8939–8944) Tellam and Eisemann's injection protocol is used (Int. J. Parasitol, 28, 439–450) where IIM is first mixed in Freund's incomplete adjuvant and then equal portions are injected intramuscular into each rear leg. A second injection is given 1 month later in the neck region. The goats are bled prior to each injection and 2 weeks after the first injection.

IIM can also be isolated from insect frass by collecting excreted PMs for the isolation of PM protein. *T.ni* larvae are reared to the fifth instar on a high wheat germ diet and then placed on diet containing sucrose and agar. Feeding insects on this diet should clear their alimentary canals of ingested high wheat germ diet and produce PMs relatively clean of dietary protein. PMs are collected, IIM solubilized and purified as described above.

To generate antibodies to chitin binding domains of PM proteins, chitin binding peptides are expressed using a baculovirus expression vector in High Five™ insect cells for optimum expression of peptides as described above. Polyclonal antibodies are produced in New Zealand White rabbits by injecting them with a total of 25–50~Ig of purified peptide. Preimmune serum is collected and used for control experiments. An antigen-capture ELISA is performed to determine the concentration of the total IgG in the original sera. To create a monoclonal antibody the antigen would be injected into a mouse and a hybridoma is created by well known methods. The gene encoding the antibody can then be isolated and used to transfect plants.

The antigen for any of the above can also be recombinant protein, which would be most useful if the desire was to target specific chitin binding sites. There are five chitin binding sites in IIM and they are depicted in FIG. 4. Anyone of these regions could be expressed in an appropriate vector, e.g. baculovirus expression system, to create antibodies that bind specifically to these regions.

Transgenic Organisms Expressing anti IIM-IgG

The present invention includes a transgenic plant that express IIM-IgG. Since the immunotherapeutic potential of antibodies produced in plants has been demonstrated in a number of cases, we believe that using peritrophic matrix IIM-specific Ab in plants could be used as immunocontrol strategy for control of insect pests. The concept of using PM Ab to control insect pest has been established in the case of insects that are animal pests. Researchers in Australia have shown that PM proteins injected into sheep produce antibodies that interfere with the growth or even kill the fly pest, *Lucilia cuprina* that causes cutaneous myiasis in the sheep, a conditions that causes over 200 million dollars in losses per year. These researcher provided evidence that the Ab were able to interfere with the porosity of the fly PM and interfered with the normal digestive processes of the insect. They speculated that this type of approach could be used in plants to control insects, however, provided not guidance as to how to accomplish such and approach.

A gene encoding an antibody that binds IIM or a fragment thereof may be used to transfect a microbial host. Microorganism hosts may be selected which are known to occupy the environment that the insect larval pest occupies. Such microorganisms include bacteria, algae, and fungi. A number of ways are known in the art for introducing a such a gene into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

A transgenic plant expressing IIM-IgG can be constructed using available techniques for inserstion of cDNA encoding an antibody to IIM into a plant genome. Referring FIG. 1, the regions designated II, IV and VI are chitin binding regions. Antibodies that bind to any of the regions would block chitin binding and provide the desired effect.

Thus the preferred first step in developing a transgenic plant is to raise one or more antibodies to the chitin binding regions. However, it could be desirable to raise an antibody that bound to a non-chitin binding region of the protein so that the chitin binding function of the protein remained intact. The antibody could then block pores in the PM but not disrupt PM formation.

Technology for using transgenic plants to express such antibodies is known in the art. Specifically, U.S. Pat. No. 5,686,600 teaches the production of antibodies that bind to insect midgut tissue and the use of such antibodies. The teaching of this patent are incorporated herein by reference. The novel IIM protein discovered by the applicants is an excellent target protein for the antibody binding.

An antibody, monoclonal antibody, or fragment thereof is said to be capable of binding a molecule if it is capable of specifically reacting with the molecule to thereby bind the molecule to the antibody, monoclonal antibody, or fragment thereof. The term "antibody" (Ab) or "monoclonal antibody" (Mab) is meant to include intact molecules as well as fragments or binding regions or domains thereof which are capable of binding to the regions described above. Such fragments are typically produced by proteolytic cleavage, such as papain or pepsin, but can be produced through the application of recombinant DNA technology or through synthetic chemistry.

Methods for the preparation of the antibodies of the present invention are generally known in the art. For example, see Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, R., et al. Monoclonal Antibodies, Hybridoma: A New Dimension in Biological Analyses, Plenum Press, N.Y. (1980); and Campbell, A. "Monoclonal Antibody Technology," In Laboratory Techniques in Biochemistry and Molecular Biology, Vol. 13, Burdon et al. (eds.), Elsevier, Amsterdam (1984). See also, U.S. Pat. Nos. 4,609,893; 4,713,325; 4,714,681; 4,716,111; 4,716,117; and 4,720,459.

The antibodies which possess the desired binding specificity can be used as a source of messenger RNA for cloning of the cDNA for the particular monoclonal antibody. Antibody genes can be cloned from hybridoma cells using primers to conserved DNA sequences within the constant regions and the framework regions of the variable regions. This can be followed by amplification of the DNA for cloning using the polymerase chain reaction (PCR). A database of mouse heavy chain and light chain sequences complied by Kabat et al. has been successfully used to generate both isotype specific and degenerate prim for cloning antibody genes (Kabat, E. A. et al., 1987, U.S. Dept Health and Human Services, U.S. Government Printing Offices and Jones, S. T. and Bendig, M., 1991, Bio/technology 9:88–89). Additionally, there is a wealth of knowledge concerning the cloning of smaller fragments of antibodies which possess the binding properties of the original antibody.

The cloned DNA can then be sequenced by methods known in the art. See, for example, Sambrook et al., Molecular Cloning: A Laboratory Manual, 2nd. Edition, Cold Spring Harbor Laboratory Press, N.Y. (1989) vol. 1–3, and the references cited therein. From the nucleic acid sequence, the protein sequence of the binding region from the selected MAb can be deduced.

The antibodies and monoclonal antibodies of the invention find use in the production of hybrid toxin molecules. By "hybrid toxin molecules" or "hybrid toxins" is intended, fusion proteins or immunotoxins, which comprise a monoclonal antibody or antibody fragment operably linked to a toxin moiety and which is capable of binding to the gut of an insect. That is, when linked, the monoclonal antibody or antibody fragment retains its binding properties and the toxin moiety retains its cytotoxic properties. DNA sequences encoding the toxin moiety of the hybrid toxins are known in the art. See, Lamb et al. (1985) Eur. J. Biochem. 148:275–170 (Ricin); Gray et al. (1984) PNAS 81:2645–2649 (Pseudomonas toxin DNA Sequence); Hindley and Berry (1988) Nuc. Acids Res. 16:4168 (*B. sphaericus* toxin gene); Bauman et al. (1988) J. Bacteriol 170:2045–2050, Bauman et al. 1987) J. Bacteriol 169:4061–4067, Berry and Hindley (1987) Nucleic Acids Res. 15:5891, Berry et al. (1989) Nucleic Acids Res. 17:7516 (*B. sphaericus*); WO 9309130-A (gelonin); EP 466222-A, U.S. Pat. No. 5,128,460 (ribosome-activating protein); EP 412911-A (barnase); Heernstadt et al. (1987) Gene 57:37–46 (cryIIIA); Brizzard and Whiteley (1988) Nucleic Acids Res 16:2723–2724 (cryIB); and Geiser et al. (1986) Gene 48:109–118 (cryIA(b)). See also Porter et al. (1993) Microbiological Reviews 57:838–861; Hofte and Whiteley (1989) Microbiological Reviews 53:242–255.

The antibody genes can be cloned and expressed in plants in such a manner that functional antibodies are assembled. See, for example, Hiatt et al. (1989) Nature 342:76–78 During et al. (1990) J. Plant Molecular Biology 15:281–293 and PCT Application WO 91/06320. Levels of bivalent antibody expression have been reported to be as high as 1% of the soluble protein in tobacco. It is recognized that as well as antibody molecules, antibody fragments such as Fab and Fv fragments, can be utilized. The use of these antibody fragments provides the option of reducing the insect specific binding domain derived from a MAb to a very small size.

The genes can be optimized for enhanced expression in plants. See, for example EPA 0359472; EPA 0385962; WO 91/16432; Perlak et al. (1991) Proc. Natl. Acad. Sci. USA 88:3324–3328;and Murray (1989) Nucleic Acids Research 17:477–498. In this manner, the genes can be synthesized utilizing plant preferred codons. That is, the preferred codon for a particular host is the single codon which most frequently encodes that amino acid in that host. Synthetic genes could also be made based on the distribution of codons a particular host uses for a particular amino acid. Following this approach, the nucleotide sequences can be optimized for expression in any plant and all or any part of the gene sequence may be optimized or synthetic.

Methods for the transformation of plant cells and regeneration of transformed plants are well known in the art. Generally, for the introduction of foreign DNA into plants Ti plasmid vectors have been utilized as well as direct DNA uptake, liposomes, electroporation, micro-injection, and the use of microprojectiles. Such methods have been published. See, for example, Guerche et al., (1987) Plant Science 52:111–116; Neuhause et al., (1987) Theor. Appl. Genet. 75:30–36; Klein et al., (1987) Nature 327:70–73; Howell et al., (1980) Science 208:1265; Horsch et al., (1985) Science 227: 1229–1231; DeBlock et al., (1989) Plant Physiology 91:694–701; Methods for Plant Molecular Biology (Weissbach and Weissbach, eds.) Academic Press, Inc. (1988); and Methods in Plant Molecular Biology (Schuler and Zielinski, eds.) Academic Press, Inc. (1989). See also, EPA 0193259 and EPA 0451878A1. It is understood that the method of transformation will depend upon the plant cell to be transformed.

The components of an expression cassette containing the sequence of interest may be modified to increase expression in the plant or plant cell For example, truncated sequences, nucleotide substitutions or other modifications may be employed. See, for example Perlak et al. (1991) Proc. Natl. Acad. Sci. USA 88:3324–3328; Murray et al. (1989) Nucleic Acids Research 17:477–498; and WO 91/16432. The construct may also include any other necessary regulators such as terminators, (Guerineau et al., (1991), Mol. Gen. Genet., 226:141–144; Proudfoot, (1991), Cell, 64:671–674; Sanfacon et al., (1991), Genes Dev., 5:141–149; Mogen et al., (1990), Plant Cell 2:1261–1272; Munroe et al., (1990), Gene, 91:151–158; Ballas et al., (1989), Nucleic Acids Res., 17:7891–7903; Joshi et al., (1987), Nucleic Acid Res., 15:9627–9639); plant translational consensus sequences (Joshi, C. P., (1987), Nucleic Acids Research, 15:6643–6653), introns (Luehrsen and Walbot, (1991), Mol. Gen. Genet., 225:81–93) and the like, operably linked to the nucleotide sequence. For tissue specific expression, the nucleotide sequences of the invention can be operably linked to tissue specific promoters.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A recombinant DNA sequence comprising a nucleic acid sequence encoding an invertebrate intestinal mucin (IIM) protein; wherein the nucleic acid sequence is selected from the group consisting of:
   a) SEQ ID NO: 1; and
   b) SEQ ID NO: 2.

2. The recombinant DNA sequence of claim 1, wherein said IIM protein has an amino acid sequence selected from the group consisting of:
   a) SEQ ID NO: 3; and
   b) SEQ ID NO: 4.

3. An expression vector containing a recombinant DNA sequence encoding *Trichoplusia ni* IIM protein.

4. The expression vector of claim 3, wherein said expression vector is a plant expression vector.

5. A transformed plant, comprising an expression vector, wherein said expression vector comprises a gene encoding a *Trichoplusia ni* invertebrate intestinal mucin (IIM) protein operably linked to an expression control sequence, such that said transformed plant is capable of expressing said IIM protein.

6. A method of producing a *Trichoplusia ni* IIM protein comprising:
   a) transforming a host cell with an expression vector comprising a promoter operably linked to a nucleotide sequence which codes for a *Trichoplusia ni* IIM protein;
   b) culturing said host cell under conditions such that said IIM protein is expressed;
   c) lysing said host cell; and
   d) recovering said IIM protein.

7. The method of claim 6 wherein said expression vector further comprises a gene encoding a transfer molecule such as glutathione-S-transferase.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 2455 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
    (A) ORGANISM: Trichoplusia ni
    (F) TISSUE TYPE: Peritrophic Membrane (vii) IMMEDIATE SOURCE:
    (B) CLONE: IIM14

(xi) SEQUENCE DESCRIPTION: SEQ ID NO:1:

```
GTAACGTTAA GTGAAAAGAA TAACCAGCGA ACAAGTTATG ATAAAGACCC TCCTATTCCT      60
GACGGCCCTC GGGCTCGTCG CCGCGCGTCC TGAAGTCAGC GACGCGGAGA AGAACCCCGC     120
TCTCCACGAG CCGCACCCAG ACTGCCCTCC CGCTGAGCAG CACTGGCTCC TGCCTCACGA     180
ATACGACTGC ACCAAGTTCT ACTACTGTGA ATATGGTCTC AAGTTCATCG CACCGAGAGA     240
CTGTGCTCCT GGTACCGAAT TCAAGTTCTC CGCTCAGACT TGTGTTCACG CCGCTTTAGC     300
CGGATGCACC CTGCCAGGAC CTCCAGCTGA GACAACCCAG GCCCCAGCAA CAACTCAGGC     360
CCCAACAACC ACCCAGGCCC CAACCACAAC TACTCAGGCC CCTACTACAA CCACCCAGGC     420
CCCAACCACA ACCACCCAGG CCCCAACCAC CACCCAGGCC CCAACCACCA CCCAGGCCCC     480
AACTACCACT CAGGCCCCTA CTACTACCAC TCAGGCCCCA ACCACAACCA CTCAGGCCCC     540
TACCACAACC ACCCAGGCCC CAACCACCAC CCAGGCCCCA ACTACCACCC AGGCCCCAAC     600
TACCACTCAG GCCCCAACTA CAATCACCCA GGCTGCAACT ACCCCGGCCG CAACTACCCC     660
GGCCGCAACT ACCCCGGCCG CAACTACCCC TGCCGCGACA ACCCCGCTG CAACTACCCC      720
AGGTGTTCCT GCACCCACTT CAGCCCCAGT CTGGCCCCCG ATCTGTGAAC TGTTGCCCAA     780
TGGTTGCCCA GCTGACTTCG ACATCCACTT GTTGATTCCC CACGACAAGT ACTGCAACCT     840
CTTCTACCAG TGCTCCAACG GTTACACCTT CGAACAGAGG TGCCCTGAGG GACTCTACTT     900
CAACCCCTAC GTCCAGCGCT GCGACTCTCC TGCTAACGTT GAATGCGACG GCGAAATCAG     960
CCCCGCACCC CCAGTCACAG AAGGCAACGA AGACGAAGAC ATTGACATCG GAGACCTCCT    1020
CGACAATGGA TGCCCAGCTA ACTTCGAAAT CGACTGGCTC TTGCCCCACG GAAACCGTTG    1080
CGACAAGTAT TACCAGTGCG TCCACGGTAA CTTGGTAGAG AGGCGTTGTG GAGCCGGCAC    1140
CCACTTCAGT TTTGAACTTC AGCAATGTGA CCACATCGAG CTCGTTGGCT GCACCCTCCC    1200
CGGCGGCGAG AGCGAAGAAG TTGACGTCGA CGAGGATGCC TGCACCGGCT GGTACTGCCC    1260
CACGGAACCC ATTGAATGGG AGCCCCTCCC CAACGGCTGC CCTGCCGACT TCAGCATCGA    1320
CCACCTCCTC CCCCACGAGA GCGACTGCGG CCAGTATCTA CAGTGTGTCC ATGGACAGAC    1380
```

-continued

```
TATCGCAAGA CCTTGCCCTG GAAACCTGCA CTTCAGTCCT GCCACACAGT CCTGTGAGTC   1440

TCCTGTGACC GCTGGTTGCC AAGTTTTCGA GTGCGATTCT GACAACCAGT GCACATCGAC   1500

TGCTGCCCCG ACAGCTGCTC CAACGGCTGC CCCAACGGCT GCCCCAACGG CTGCCCCAAC   1560

TGCCGCACCC TCCACCGTGG TCCCACCTGC AACGCCACCC GCAACTGCAG CCCCAGTCCC   1620

ACCTACAACC GCAATTCCTA CTCCGGCCCC CACCGCTGCC CCCACCGCAG CTCCTACTAC   1680

TGCTGCCCCT GAATCCCCAA CCACTGTCAC AGTACCACCT ACTGCTGCTC CCACCGCAGC   1740

CCCTACTACT GCTGTCCCTG AAATCCCAAT CACTGTCACA TCAGCGCCTA CCGCTGCCCC   1800

CACCGCTGCC CCCACCGCTG CCCCCACCGC AGCCCCTACT ACTGCTGTCC CAGAAATCCC   1860

AACTACTGTC ACATCACCAC CTACTGCTGC CCCCACTACC GCAGCACCTG CCCCAACAC   1920

CACAGTCACT GTACCACCCA CTGCTGCCCC TACTACCGCA GCACCTGCCC CCAACACCAC   1980

AGTCACTGTA CCACCCACTG CTGCCCCCAC TGCAGCTCCC CCTACCGTCG CACATGCACC   2040

CAACACCACA GCTGCCCCGG TAACTACAAC CAGCGCACCA GCTACCACAC CTGAAGATGA   2100

TGACATCGAC CCCCCTCTCC CCAACGACCC CATCAACCCT TGCGTTGAAG AATGCAACGT   2160

TTTGCCCTGG GCTCACGCTG ACTGCGACAA ATACTGGGTC TGTGACGGCA CAACCAAGT   2220

CCTGGTGGTT TGCTCTGAGG GTCTCCAGTT CAACCCCACT ACTAAGACCT GTGACTTCGC   2280

TTGCAACGTC GGTTGCGTGA GGAGCAACAT TCAGATGTCT GAAAGCTACG AAGGAGTCCA   2340

GGTCTTCATC CCATGGAACA AACTAGATGA AGACATCAGA CAGGCGCTGA ACTTTGAGTT   2400

GTAAACCTAC TTAAATTAAT GAAGGTTTTG TTTTAAAAAA AAAAAAAAAA AAAAA         2455
```

(2) INFORMATION FOR SEQ ID NO:2:

(i) SEQUENCE CHARACTERISTICS:
        (A) LENGTH: 2821 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: Trichoplusia ni
        (D) DEVELOPMENTAL STAGE: larva
        (F) TISSUE TYPE: peritrophic membrane (xi) SEQUENCE DESCRIPTION: SEQ ID NO:2:

```
GAAAAGAATA ACCAGCGAAC AAGTTATGAT AAAGACCCTC CTATTCCTGA CGGCCCTCGG     60

GCTCGTCGCC GCGCGTCCTG AAGTCAGCGA CGCGGAGAAG AACCCCGCTC TCCACGAGCC    120

GCACCCAGAC TGCCCTCCCG CTGAGCAGCA CTGGCTCCTG CCTCACGAAT ACGACTGCAC    180

CAAGTTCTAC TACTGTGAAT ATGGTCTCAA GTTCATCGCA CCGAGAGACT GTGCTCCTGG    240

TACCGAATTC AAGTTCTCCG CTCAGACTTG TGTTCACGCC GCTTTAGCCG GATGCACCCT    300

GCCAGGACCT CCAGCTGAGA CAACCCAGGC CCCAGCAACA ACTCAGGCCC AACAACCAC     360

CCAGGCCCCA ACCACAACTA CTCAGGCCCC TACTACAACC ACCCAGGCCC AACCACAAC     420

CACCCAGGCC CCAACCACCA CCCAGGCCCC AACCACCACC CAGGCCCCAA CTACCACTCA    480

GGCCCCTACT ACTACCACTC AGGCCCCAAC CACAACCACT CAGGCCCCTA CCACAACCAC    540

CCAGGCCCCA ACCACCACCC AGGCCCCAAC TACCACCCAG GCCCCAACTA CCACTCAGGC    600
```

```
CCCAACTACA ATCACCCAGG CTGCAACTAC CCCGGCCGCA ACTACCCCGG CCGCAACTAC    660

CCCGGCCGCA ACTACCCCTG CCGCGACAAC CCCCGCTGCA ACTACCCCAG GTGTTCCTGC    720

ACCCACTTCA GCCCCAGTCT GGCCCCCGAT CTGTGAACTG TTGCCCAATG GTTGCCCAGC    780

TGACTTCGAC ATCCACTTGT TGATTCCCCA CGACAAGTAC TGCAACCTCT TCTACCAGTG    840

CTCCAACGGT TACACCTTCG AACAGAGGTG CCCTGAGGGA CTCTACTTCA ACCCCTACGT    900

CCAGCGCTGC GACTCTCCTG CTAACGTTGA ATGCGACGGC GAAATCAGCC CCGCACCCCC    960

AGTCACAGAA GGCAACGAAG ACGAAGACAT TGACATCGGA GACCTCCTCG ACAATGGATG   1020

CCCAGCTAAC TTCGAAATCG ACTGGCTCTT GCCCCACGGA AACCGTTGCG ACAAGTATTA   1080

CCAGTGCGTC CACGGTAACT TGGTAGAGAG GCGTTGTGGA GCCGGCACCC ACTTCAGTTT   1140

TGAACTTCAG CAATGTGACC ACATCGAGCT CGTTGGCTGC ACCCTCCCCG GCGGCGAGAG   1200

CGAAGAAGTT GACGTCGACG AGGATGCCTG CACCGGCTGG TACTGCCCCA CGGAACCCAT   1260

TGAATGGGAG CCCCTCCCCA ACGGCTGCCC TGCCGACTTC AGCATCGACC ACCTCCTCCC   1320

CCACGAGAGC GACTGCGGCC AGTATCTACA GTGTGTCCAT GGACAGACTA TCGCAAGACC   1380

TTGCCCTGGA AACCTGCACT TCAGTCCTGC CACACAGTCC TGTGAGTCTC CTGTGACCGC   1440

TGGTTGCCAA GTTTTCGAGT GCGATTCTGA CAACCAGTGC ACATCGACTG CTGCCCCGAC   1500

AGCTGCTCCA ACGGCTGCCC CAACGGCTGC CCCAACGGCT GCCCCAACTG CCGCACCCTC   1560

CACCGTGGTC CCACCTGCAA CGCCACCCGC AACTGCAGCC CCAGTCCCAC CTACAACCGC   1620

AATTCCTACT CCGGCCCCCA CCGCTGCCCC CACCGCAGCT CCTACTACTG CTGCCCCTGA   1680

ATCCCCAACC ACTGTCACAG TACCACCTAC TGCTGCTCCC ACCGCAGCCC CTACTACTGC   1740

TGTCCCTGAA ATCCCAATCA CTGTCACATC AGCGCCTACC GCTGCCCCCA CCGCTGCCCC   1800

CACCGCTGCC CCCACCGCAG CCCCTACTAC TGCTGTCCCA GAAATCCCAA CTACTGTCAC   1860

ATCACCACCT ACTGCTGCCC CCACTACCGC AGCACCTGCC CCAACACCA CAGTCACTGT   1920

ACCACCCACT GCTGCCCCTA CTACCGCAGC ACCTGCTCCC AACACCACAG TGACTGCACC   1980

ACCCACCGCA GCCCTACTA CCGCAGCACC TGCCCCCAAC ACCACAGTCA CTGTACCACC   2040

CACTGCTGCC CCCACTGCAG CTCCCCCTAC CGTCGCACCT GCACCCAACA CCACAGCTGC   2100

CCCGGTAACT ACAACCAGCG CACCAGCTAC CACACCTGAA GATGATGACA TCGACCCCCC   2160

TCTCCCCAAC GACCCCATCA ACCCTTGCGT TGAAGAATGC AACGTTTTGC CCTGGGCTCA   2220

CGCTGACTGC GACAAATACT GGGTCTGTGA CGGCAACAAC CAAGTCCTGG TGGTTTGCTC   2280

TGAGGGTCTC CAGTTCAACC CCACTACTAA GACCTGTGAC TTCGCTTGCA ACGTCGGTTG   2340

CGTGAGGAGC AACATTCAGA TGTCTGAAAG CTACGAAGGA GTCCAGGTCT TCATCCCATG   2400

GAACAAACTA GATGAAGACA TCAGACAGGC GCTGAACTTT GAGTTGTAAA CCTACTTAAA   2460

TTAATGAAGG TTTTGTTTTA TTTTTGAGTT ATTATTCCAA TGGGCGGGAA AGTCCGCCAT   2520

TATTGGGTCT TGCCAGTTTT GAGGAAACCT TTTTTTTTAC TACCAACATT CTTGTGAACC   2580

CATATTTATT ACGTATTAAA CATCGTGATT TGAAAAACGT TACATGATTT TTTCATTAAT   2640

TTGAAACAAT TTATGTTGTT TTTGTTCTCA TTAAATATCA AATATCATTT TCGAAACTGG   2700

CAATTTTGGA TTGGAATAAT CAACAAATGG TTAAGAAAAA AAACGATTTC TTAAAAATGT   2760

ATTTATTATA AAATGTGTAA ATAAATATAC AAATTAGCAT TTAAAAAAAA AAAAAAAAA   2820

A                                                                  2821
```

(2) INFORMATION FOR SEQ ID NO:3:

```
    (i) SEQUENCE CHARACTERISTICS:
        (A) LENGTH: 788 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Trichoplusia ni
        (F) TISSUE TYPE: peritrophic membrane (xi) SEQUENCE DESCRIPTION: SEQ ID NO:3:

Met Ile Lys Thr Leu Leu Phe Leu Thr Ala Leu Gly Leu Val Ala Ala
1               5                   10                  15

Arg Pro Glu Val Ser Asp Ala Glu Lys Asn Pro Ala Leu His Glu Pro
            20                  25                  30

His Pro Asp Cys Pro Pro Ala Glu Gln His Trp Leu Leu Pro His Glu
        35                  40                  45

Tyr Asp Cys Thr Lys Phe Tyr Tyr Cys Glu Tyr Gly Leu Lys Phe Ile
    50                  55                  60

Ala Pro Arg Asp Cys Ala Pro Gly Thr Glu Phe Lys Phe Ser Ala Gln
65                  70                  75                  80

Thr Cys Val His Ala Ala Leu Ala Gly Cys Thr Leu Pro Gly Pro Pro
                85                  90                  95

Ala Glu Thr Thr Gln Ala Pro Ala Thr Thr Gln Ala Pro Thr Thr Thr
            100                 105                 110

Gln Ala Pro Thr Thr Thr Thr Gln Ala Pro Thr Thr Thr Thr Gln Ala
        115                 120                 125

Pro Thr Thr Thr Thr Gln Ala Pro Thr Thr Thr Gln Ala Pro Thr Thr
    130                 135                 140

Thr Gln Ala Pro Thr Thr Thr Gln Ala Pro Thr Thr Thr Thr Gln Ala
145                 150                 155                 160

Pro Thr Thr Thr Thr Gln Ala Pro Thr Thr Thr Thr Gln Ala Pro Thr
                165                 170                 175

Thr Thr Gln Ala Pro Thr Thr Thr Gln Ala Pro Thr Thr Thr Gln Ala
            180                 185                 190

Pro Thr Thr Ile Thr Gln Ala Ala Thr Thr Pro Ala Ala Thr Thr Pro
        195                 200                 205

Ala Ala Thr Thr Pro Ala Ala Thr Thr Pro Ala Ala Thr Thr Pro Ala
    210                 215                 220

Ala Thr Thr Pro Gly Val Pro Ala Pro Thr Ser Ala Pro Val Trp Pro
225                 230                 235                 240

Pro Ile Cys Glu Leu Leu Pro Asn Gly Cys Pro Ala Asp Phe Asp Ile
                245                 250                 255

His Leu Leu Ile Pro His Asp Lys Tyr Cys Asn Leu Phe Tyr Gln Cys
            260                 265                 270

Ser Asn Gly Tyr Thr Phe Glu Gln Arg Cys Pro Glu Gly Leu Tyr Phe
        275                 280                 285

Asn Pro Tyr Val Gln Arg Cys Asp Ser Pro Ala Asn Val Glu Cys Asp
    290                 295                 300

Gly Glu Ile Ser Pro Ala Pro Pro Val Thr Glu Gly Asn Glu Asp Glu
305                 310                 315                 320
```

-continued

```
Asp Ile Asp Ile Gly Asp Leu Asp Asn Gly Cys Pro Ala Asn Phe
            325                 330                 335

Glu Ile Asp Trp Leu Leu Pro His Gly Asn Arg Cys Asp Lys Tyr Tyr
                340                 345                 350

Gln Cys Val His Gly Asn Leu Val Glu Arg Arg Cys Gly Ala Gly Thr
            355                 360                 365

His Phe Ser Phe Glu Leu Gln Gln Cys Asp His Ile Glu Leu Val Gly
    370                 375                 380

Cys Thr Leu Pro Gly Gly Glu Ser Glu Glu Val Asp Val Asp Glu Asp
385                 390                 395                 400

Ala Cys Thr Gly Trp Tyr Cys Pro Thr Glu Pro Ile Glu Trp Glu Pro
                405                 410                 415

Leu Pro Asn Gly Cys Pro Ala Asp Phe Ser Ile Asp His Leu Leu Pro
            420                 425                 430

His Glu Ser Asp Cys Gly Gln Tyr Leu Gln Cys Val His Gly Gln Thr
        435                 440                 445

Ile Ala Arg Pro Cys Pro Gly Asn Leu His Phe Ser Pro Ala Thr Gln
    450                 455                 460

Ser Cys Glu Ser Pro Val Thr Ala Gly Cys Gln Val Phe Glu Cys Asp
465                 470                 475                 480

Ser Asp Asn Gln Cys Thr Ser Thr Ala Ala Pro Thr Ala Ala Pro Thr
            485                 490                 495

Ala Ala Pro Thr Ala Ala Pro Thr Ala Ala Pro Thr Ala Ala Pro Ser
            500                 505                 510

Thr Val Val Pro Pro Ala Thr Pro Pro Ala Thr Ala Ala Pro Val Pro
        515                 520                 525

Pro Thr Thr Ala Ile Pro Thr Pro Ala Pro Thr Ala Ala Pro Thr Ala
    530                 535                 540

Ala Pro Thr Thr Ala Ala Pro Glu Ser Pro Thr Thr Val Thr Val Pro
545                 550                 555                 560

Pro Thr Ala Ala Pro Thr Ala Ala Pro Thr Thr Ala Val Pro Glu Ile
            565                 570                 575

Pro Ile Thr Val Thr Ser Ala Pro Thr Ala Ala Pro Thr Ala Ala Pro
        580                 585                 590

Thr Ala Ala Pro Thr Ala Ala Pro Thr Thr Ala Val Pro Glu Ile Pro
    595                 600                 605

Thr Thr Val Thr Ser Pro Pro Thr Ala Ala Pro Thr Thr Ala Ala Pro
610                 615                 620

Ala Pro Asn Thr Thr Val Thr Val Pro Pro Thr Ala Ala Pro Thr Thr
625                 630                 635                 640

Ala Ala Pro Ala Pro Asn Thr Thr Val Thr Val Pro Pro Thr Ala Ala
            645                 650                 655

Pro Thr Ala Ala Pro Pro Thr Val Ala His Ala Pro Asn Thr Thr Ala
            660                 665                 670

Ala Pro Val Thr Thr Thr Ser Ala Pro Ala Thr Thr Pro Glu Asp Asp
        675                 680                 685

Asp Ile Asp Pro Pro Leu Pro Asn Asp Pro Ile Asn Pro Cys Val Glu
    690                 695                 700

Glu Cys Asn Val Leu Pro Trp Ala His Ala Asp Cys Asp Lys Tyr Trp
705                 710                 715                 720

Val Cys Asp Gly Asn Asn Gln Val Leu Val Val Cys Ser Glu Gly Leu
            725                 730                 735

Gln Phe Asn Pro Thr Thr Lys Thr Cys Asp Phe Ala Cys Asn Val Gly
```

-continued

```
                       740                 745                 750
Cys Val Arg Ser Asn Ile Gln Met Ser Glu Ser Tyr Glu Gly Val Gln
            755                 760                 765
Val Phe Ile Pro Trp Asn Lys Leu Asp Glu Asp Ile Arg Gln Ala Leu
            770                 775                 780
Asn Phe Glu Leu
785
```

(2) INFORMATION FOR SEQ ID NO:4:

(i) SEQUENCE CHARACTERISTICS:
        (A) LENGTH: 807 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Trichoplusia ni
        (F) TISSUE TYPE: peritrophic membrane (xi) SEQUENCE DESCRIPTION: SEQ ID NO:4:

```
Met Ile Lys Thr Leu Leu Phe Leu Thr Ala Leu Gly Leu Val Ala Ala
1               5                   10                  15
Arg Pro Glu Val Ser Asp Ala Glu Lys Asn Pro Ala Leu His Glu Pro
            20                  25                  30
His Pro Asp Xaa Pro Pro Ala Glu Gln Xaa Xaa Leu Leu Pro Xaa Glu
            35                  40                  45
Tyr Asp Cys Thr Lys Phe Tyr Tyr Cys Glu Tyr Gly Leu Lys Phe Ile
        50                  55                  60
Ala Pro Arg Asp Cys Ala Pro Gly Thr Glu Phe Lys Phe Ser Ala Gln
65                  70                  75                  80
Thr Cys Val His Ala Ala Leu Ala Gly Cys Thr Leu Pro Gly Pro Pro
                85                  90                  95
Ala Glu Thr Thr Gln Ala Pro Ala Thr Thr Gln Ala Pro Thr Thr Thr
            100                 105                 110
Gln Ala Pro Thr Thr Thr Gln Ala Pro Thr Thr Thr Gln Ala Pro Thr
            115                 120                 125
Pro Thr Thr Thr Gln Ala Pro Thr Thr Thr Gln Ala Pro Thr Thr Thr
        130                 135                 140
Thr Gln Ala Pro Thr Thr Thr Gln Ala Pro Thr Thr Thr Gln Ala Pro
145                 150                 155                 160
Pro Thr Thr Thr Gln Ala Pro Thr Thr Thr Gln Ala Pro Thr Thr Thr
                165                 170                 175
Thr Thr Gln Ala Pro Thr Thr Thr Gln Ala Pro Thr Thr Thr Gln Ala
            180                 185                 190
Pro Thr Thr Ile Thr Gln Ala Ala Thr Thr Pro Ala Ala Thr Thr Pro
            195                 200                 205
Ala Ala Thr Thr Pro Ala Ala Thr Thr Pro Ala Ala Thr Thr Pro Ala
        210                 215                 220
Ala Thr Thr Pro Gly Val Pro Ala Pro Thr Ser Ala Pro Val Trp Pro
225                 230                 235                 240
Pro Ile Cys Glu Leu Leu Pro Asn Gly Cys Pro Ala Asp Phe Asp Ile
                245                 250                 255
```

-continued

```
His Leu Leu Ile Pro His Asp Lys Tyr Cys Asn Leu Phe Tyr Gln Cys
            260                 265                 270

Ser Asn Gly Tyr Thr Phe Glu Gln Arg Cys Pro Glu Gly Leu Tyr Phe
        275                 280                 285

Asn Pro Tyr Val Gln Arg Cys Asp Ser Pro Ala Asn Val Glu Cys Asp
    290                 295                 300

Gly Glu Ile Ser Pro Ala Pro Val Thr Glu Gly Asn Glu Asp Glu
305                 310                 315                 320

Asp Ile Asp Ile Gly Asp Leu Leu Asp Asn Gly Cys Pro Ala Asn Phe
                325                 330                 335

Glu Ile Asp Trp Leu Leu Pro His Gly Asn Arg Cys Asp Lys Tyr Tyr
            340                 345                 350

Gln Cys Val His Gly Asn Leu Val Glu Arg Arg Cys Gly Ala Gly Thr
        355                 360                 365

His Phe Ser Phe Glu Leu Gln Gln Cys Asp His Ile Glu Leu Val Gly
    370                 375                 380

Cys Thr Leu Pro Gly Gly Glu Ser Glu Glu Val Asp Val Asp Glu Asp
385                 390                 395                 400

Ala Cys Thr Gly Trp Tyr Cys Pro Thr Glu Pro Ile Glu Trp Glu Pro
                405                 410                 415

Leu Pro Asn Gly Cys Pro Ala Asp Phe Ser Ile Asp His Leu Leu Pro
            420                 425                 430

His Glu Ser Asp Cys Gly Gln Tyr Leu Gln Cys Val His Gly Gln Thr
        435                 440                 445

Ile Ala Arg Pro Cys Pro Gly Asn Leu His Phe Ser Pro Ala Thr Gln
    450                 455                 460

Ser Cys Glu Ser Pro Val Thr Ala Gly Cys Gln Val Phe Glu Cys Asp
465                 470                 475                 480

Ser Asp Asn Gln Cys Thr Ser Thr Ala Ala Pro Thr Ala Ala Pro Thr
                485                 490                 495

Ala Ala Pro Thr Ala Ala Pro Thr Ala Ala Pro Thr Ala Ala Pro Ser
            500                 505                 510

Thr Val Val Pro Pro Ala Thr Pro Pro Ala Thr Ala Ala Pro Val Pro
        515                 520                 525

Pro Thr Thr Ala Ile Pro Thr Pro Ala Pro Thr Ala Ala Pro Thr Ala
    530                 535                 540

Ala Pro Thr Thr Ala Ala Pro Glu Ser Pro Thr Thr Val Thr Val Pro
545                 550                 555                 560

Pro Thr Ala Ala Pro Thr Ala Ala Pro Thr Thr Ala Val Pro Glu Ile
                565                 570                 575

Pro Ile Thr Val Thr Ser Ala Pro Thr Ala Ala Pro Thr Ala Ala Pro
            580                 585                 590

Thr Ala Ala Pro Thr Ala Ala Pro Thr Ala Val Pro Glu Ile Pro
        595                 600                 605

Thr Thr Val Thr Ser Pro Pro Thr Ala Ala Pro Thr Thr Ala Ala Pro
    610                 615                 620

Ala Pro Asn Thr Thr Val Thr Val Pro Pro Thr Ala Ala Pro Thr Thr
625                 630                 635                 640

Ala Ala Pro Ala Pro Asn Thr Thr Val Thr Ala Pro Pro Thr Ala Ala
                645                 650                 655

Pro Thr Thr Ala Ala Pro Ala Pro Asn Thr Thr Val Thr Val Pro Pro
            660                 665                 670
```

-continued

```
Thr Ala Ala Pro Thr Ala Ala Pro Pro Thr Val Ala His Ala Pro Asn
        675             680             685

Thr Thr Ala Ala Pro Val Thr Thr Thr Ser Ala Pro Ala Thr Thr Pro
    690             695             700

Glu Asp Asp Asp Ile Asp Pro Pro Leu Pro Asn Asp Pro Ile Asn Pro
705             710             715                     720

Cys Val Glu Glu Cys Asn Val Leu Pro Trp Ala His Ala Asp Cys Asp
            725             730                 735

Lys Tyr Trp Val Cys Asp Gly Asn Asn Gln Val Leu Val Cys Ser
            740             745             750

Glu Gly Leu Gln Phe Asn Pro Thr Thr Lys Thr Cys Asp Phe Ala Cys
        755             760             765

Asn Val Gly Cys Val Arg Ser Asn Ile Gln Met Ser Glu Ser Tyr Glu
    770             775             780

Gly Val Gln Val Phe Ile Pro Trp Asn Lys Leu Asp Glu Asp Ile Arg
785             790             795                     800

Gln Ala Leu Asn Phe Glu Leu
                805
```